US006426095B2

(12) United States Patent
Palmere et al.

(10) Patent No.: US 6,426,095 B2
(45) Date of Patent: *Jul. 30, 2002

(54) METHODS AND COMPOSITIONS FOR RETARDING AND ERADICATING INFESTATION IN TREES AND TREE DERIVED PRODUCTS

(75) Inventors: Vincent R. Palmere, Knoxville; Allan H. Dietrich, Corryton; Stanley D. Galyon, Maynardville, all of TN (US)

(73) Assignee: Nisus, Corp., Rockford, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/888,875

(22) Filed: Jun. 25, 2001

Related U.S. Application Data

(60) Continuation of application No. 09/658,899, filed on Sep. 11, 2000, now abandoned, which is a continuation of application No. 08/616,654, filed on Mar. 15, 1996, now abandoned, which is a division of application No. 08/465,434, filed on Jun. 5, 1995, now Pat. No. 5,645,828, which is a division of application No. 08/213,108, filed on Mar. 14, 1994, now Pat. No. 5,460,816, which is a division of application No. 07/847,345, filed on Mar. 6, 1992, now Pat. No. 5,296,240, which is a division of application No. 07/528,838, filed on May 24, 1990, now Pat. No. 5,104,664.

(51) Int. Cl.$^7$ .......................... A61K 33/22; A01N 59/14
(52) U.S. Cl. ..................... 424/657; 424/657; 424/658; 424/659; 424/660
(58) Field of Search ................................ 424/657, 658, 424/659, 660

(56) References Cited

U.S. PATENT DOCUMENTS

| | | | |
|---|---|---|---|
| 2,968,590 A | 1/1961 | Ploquin | 167/14 |
| 2,998,310 A | 8/1961 | O'Brien | 71/2.2 |
| 3,099,598 A | 7/1963 | Birkner et al. | 167/38.5 |
| 3,305,298 A * | 2/1967 | Chapman et al. | 424/658 |
| 3,325,298 A | 6/1967 | Brown | 106/52 |
| 3,376,144 A | 4/1968 | Stutz | 106/15 |
| 3,378,381 A | 4/1968 | Draganov | 106/15 |
| 3,531,278 A | 9/1970 | Nies | 71/128 |
| 3,674,458 A * | 7/1972 | Schattner | 424/460 |
| 3,706,161 A | 12/1972 | Jenson | 47/57.5 |
| 3,812,251 A | 5/1974 | Mima et al. | 424/148 |
| 3,993,752 A | 11/1976 | Stutz | 424/129 |
| 4,076,871 A | 2/1978 | Short et al. | 427/397 |
| 4,269,875 A | 5/1981 | Bechgaard et al. | 427/291 |
| 4,291,497 A | 9/1981 | Mamankov | 47/58 |
| 4,303,726 A | 12/1981 | Turner | 427/297 |
| 4,373,010 A | 2/1983 | Oberley | 428/532 |
| 4,400,298 A | 8/1983 | Boocock et al. | 252/400 R |
| 4,461,721 A | 7/1984 | Goettsche et al. | 252/607 |
| 4,536,306 A | 8/1985 | Horodsky et al. | 252/32.7 |
| 4,610,381 A * | 9/1986 | Bechgaard | 424/148 |
| 4,610,881 A | 9/1986 | Bechgaard | 424/148 |
| 4,620,990 A | 11/1986 | Dicker | 427/291 |
| 4,719,110 A | 1/1988 | Patel et al. | 424/148 |
| 4,761,179 A | 8/1988 | Goetsche | 106/18.32 |
| 4,801,404 A | 1/1989 | Dietrich et al. | 252/607 |
| 5,017,620 A | 5/1991 | Grassman et al. | 514/698 |
| 5,061,698 A * | 10/1991 | Malouf et al. | 424/659 |
| 5,094,028 A | 3/1992 | Hume | 43/132.1 |
| 5,104,664 A * | 4/1992 | Palmere et al. | 424/660 |
| 5,129,946 A | 7/1992 | Evans | 106/18.3 |
| 5,151,127 A | 9/1992 | Thompson | 106/15.05 |
| 5,296,240 A | 3/1994 | Palmere et al. | 424/660 |
| 5,460,816 A | 10/1995 | Palmere et al. | 424/405 |
| 5,525,147 A * | 6/1996 | Dunstan et al. | |
| 5,564,222 A | 10/1996 | Brody | 43/124 |
| 5,592,774 A | 1/1997 | Galyon | 43/124 |
| 5,645,828 A * | 7/1997 | Palmere et al. | 424/78.08 |

FOREIGN PATENT DOCUMENTS

| | | | |
|---|---|---|---|
| EP | 103359 | | 3/1984 |
| EP | 46380 | | 4/1985 |
| GB | 937766 | | 9/1963 |
| GB | 1254504 | | 11/1971 |
| GB | 2088211 A | * | 1/1982 |
| GB | 2088211 | * | 6/1982 |
| JP | 58-163605 | | 9/1983 |

OTHER PUBLICATIONS

C. Abstract of Japan 03223205 A, Nov. 1991.*
Chem. & Eng. News Nov. 14, 1988 pp. 10–19.*
International Research Group on Wood Preservation, "Borates as Wood Preserving Compounds: The Status of Research in the United States," Barnes et al., Mar. 1989.
International Research Group on Wood Preservation, "Termite Resistance of Treated Wood in an Above Ground Field Teat," Preston et al., pp. 30–32, Mar. 15, 1985.
International Research Group on Wood Preservation, "Utilization of Curcumin for Detection of Presence of Boron in Wood," Marie–Louise Edlund, Feb. 1982.
*The Sri Lanka Forester,* "The Threshold Level of Boron Preservatives Against Attack by the Dry–Wood Termite—*Cyptotermes Domesticus*—Kalotermitidae," vol. 12, No. 2, Tisseverasinghe et al., Jul.–Dec., 1975.
*Forest Products Journal,* "Treatment of Log–Home Logs with Thickened Boron,"Puettmann, et al., pp. 30–32, vol. 42, No. 11/12, Nov/Dec. 1992.
Reports for Batch Nos. 1001–1010 of a formulation made from ethylene glycol, Tim–Bor, and water by the original corporate patent owner, Jun.–Nov., 1988.
Selected invoices showing that the formulation of ethylene glycol, Tim–Bor, and water made in Batch Nos. 1001–1010 were sold during Aug.–Nov., 1988.

(List continued on next page.)

*Primary Examiner*—Carlos Azpuru
(74) *Attorney, Agent, or Firm*—Merchant & Gould

(57) ABSTRACT

The present invention relates to compositions and their methods of manufacture and use which are effective for delivering a homogeneous distribution of a boron containing active ingredient to a tree or tree derived substrate for the purpose of preventing or eradicating an infestation and/or for imparting flame retardency thereto.

39 Claims, No Drawings-

OTHER PUBLICATIONS

*Log Home Guide for Builders and Buyers,* "Rest Assured" advertisement listing the patent owner's Bora–Care product, p. 243, Jan./Feb. 1989.

Letter from original corporate patent owner to Mr. Don Turner of the U.S.S. Constitution addressing the Bora–Care product, dated Apr. 3, 1989.

Follow–up letter from original corporate patent owner to Mr. Don Turner of the U.S.S. Constitution addressing the Bora–Care product, dated Jun. 7, 1989.

Letter from original corporate patent owner to Mr. Scott Dombrosky of Naval Facilities Engineering Command addressing the Bora–Care product, Aug. 19, 1989.

Letter from original corporate patent owner to Mr. Charles Stayton of the Texas Agricultural Extension Service addressing the Bora–Care product, dated Mar. 14, 1989.

Letter from original corporate patent owner to Mr. Donald Schultz of the National Park Service addressing the Bora––Care product, dated Apr. 18, 1989.

Letter from original corporate patent owner to Mr. Jim Rock of J. Rock Associates addressing the Bora–Care product, dated Apr. 19, 1989.

Letter from original corporate patent owner to Mr. Alan Perkinson of U.S. Borax & Chemical Company addressing the Bora–Care product, dated Apr. 7, 1989.

Letter from Innovative Marketing to the original corporate patent owner addressing the Bora–Care product, dated Mar. 1, 1989.

*Forest Products Journal,* "Termiticidal Effects of a Glycol Borate Wood Surface Treatment," J. Kenneth Grace et al., Nov./Dec. 1992.

*Mother Earth News,* "Safe Termite Control," Karla Harby, pp. 80–83, Mar./Apr. 1988.

*Muir's Original Log Home Guide for Builders and Buyers,* "New Treatment Available for Insect Control" Nov./Dec. 1989.

*Northeast Edition Woodshop News,* "Tenn. Firm Markets Borate Preservative," p. 16, Mar. 1990.

PCT, "Pre–Treat Woes: What's the Solution," pp. 44, 45, & 48, Mar. 1990.

*Practical Homeowner,* "Borate–Treated Wood," Don Best, pp. 22 & 24, Oct. 1989.

*Practical Homeowner,* "New Borate Treatment," p. 14, Mar. 1990.

*The Journal of Light Construction—Eight Penny News,* "Nontoxic Alternative to CCA," Don Best, vol. 8, No. 5, Feb. 1990.

*USDA Forest Service,* "Treated Test House Field Exposure Evaluations Research and Technology Transfer Demonstration Project" Williams et al. (undated).

*USDA Forest Service,* "Protect Your Wood with Borates," Sep. 1987.

*USDA Forest Service,* "Borates for Wood Protection–Evaluating Test Houses Built with Borate Treated Wood in Mississippi," Jan. 1990.

Abstract of Japan 032323205, A2, Nov. 1991.

Abstract of Soviet Japan SU 649,739 (1979), entitled "Industrial Lubricant for Cold Working Metals by Pressure."

Abstract of Japanese Patent JP 4,6031,847 (1971), entitled "Surface Active Borates."

Abstract of German Patent DE 2,831,538 (1980), entitled "Brake Fluids for Motor Vehicles."

Abstract of German Patent DE 2,438,038 (1975), entitled "Brake Fluids for Motor Vehicles."

Abstract of Polish Patent PL 126,504 B1 (1985), entitled "Wood Preservatives."

"A Test of 'Boracol,' A New Formulation Containing Borates For the Diffusion Treatment of Lumber," Johnston et al., May 1986.

*USDA Forest Service,* "Borates Offer Effective Protection with Less Hazard to the Environment," Jan. 1990.

*International Research Group on Wood Preservation,* "A Chemical and Mycological Evaluation of Fused Borate Rods and a Borate/Glycol Solution for Remedial Treatment of Window Joinery," Edlund et al., Mar. 15, 1983.

*British Wood Preserving Association,* "Borate Diffusion Techniques for the In–Situ Treatment of Joinery," Dicker et al., Jun. 1983.

*South African Wood Preservers Assoc.,* "Boron Compounds in Wood Preservation," Len T. Arthur, Sep. 1993.

*Commonwealth Sci. Ind. Res. Org. (Australia),* "Laboratory Studies of Termite Resistance: III. A Comparative Study of Anti–Termitic Value of Boric Acid, Zinc Chloride, and 'Tanalith U,'" Gay et al., Dec. 1957.

*USDA Forest Service,* "Lead Cooperative Research on Integrated Protection of Solid and Composite Wood Building Components Against Damage by Insects, Fungi, and Fire with Borate Treatments," Lonnie H. Williams, Dec. 2, 1985.

*International Search Group on Wood Preservation,* "Remedial Wood Preservative Efficacy of Bora–Care Against the Formosan Subterranean Termite and Eastern Subterranean Termite (Isoptera: Rhinotermitidae)," Nan–Yao Su et al., Apr. 2, 1991.

*1990 Annual Buyers Guide Log Home Living,* "A New Borate–based Preservative for Dry Wood and Existing Homes," p. 80, 1990 (month unknown).

*American Wood–Preserves' Association Standard,* "All Timber Products—Preservative Treatment by Pressure Processes," (date unknown).

*Back Home in the Kentucky,* "Perma–Chink Introduces Bora–Care," p. 17, Jan./Feb. 1990.

*Chem. Abstract,* vol. 104:87706x, Mar. 17, 1986.

*Chemical Engineer News,* "Preserving the Past," pp. 10–19, Nov. 14, 1988.

*Forest Products Journal,* "Integrated Protection Against Lyctid Beetle Infestations. IV Resistance of Boron–Treated Wood (Virola spp.) To Insect and Fungal Attack," Lonnie H. Williams et al., vol. 37, No. 2, Feb. 1987.

* cited by examiner

METHODS AND COMPOSITIONS FOR RETARDING AND ERADICATING INFESTATION IN TREES AND TREE DERIVED PRODUCTS

The present application is a continuation application of U.S. patent application Ser. No. 09/658,899 filed Sep. 11, 2000, now abandoned, which is a continuation application of U.S. patent application Ser. No. 08/616,654 filed Mar. 15, 1996, now abandoned, which is a divisional application of U.S. patent application Ser. No. 08/465,434 filed June 5, 1995, now U.S. Pat. No. 5,645,820 which is a divisional application of U.S. patent application Ser. No. 08/213,108 filed Mar. 14, 1994, now U.S. Pat. No. 5,460,816, which is a divisional application of U.S. patent application Ser. No. 07/847,345 filed Mar. 6, 1992, now U.S. Pat. No. 5,296,240, which is a divisional application of U.S. patent application Ser. No. 07/528,838 filed May 24, 1990, now U.S. Pat. No. 5,104,664, the benefit of which is claimed under 35 U.S.C. §120.

FIELD OF THE INVENTION

The present invention relates to compositions for use with living trees, cut timber or lumber, and other wood based products. These compositions provide protection and relief from infestation such as insects and fungi. Methods of using these composites are also contemplated.

BACKGROUND OF THE INVENTION

While lumber and other wood based products derived from trees are not perishable, they are, nevertheless, susceptible to a host of natural destructive forces. These primarily include attack by insects, such as termites, carpenter ants and the like and fungi such as brown (Poria Sp.) and white (Polyporous Sp.) wood decay fungi (*Poria Incrassata*). Living, growing trees are also subject to attack from insects and fungi.

Many protective treatments have been developed for the protection of lumber and other tree derived products. For example, Bechgaard, U.S. Pat. No. 4,610,881 relates to a protective composition with a penetrating carrier which comprises a mixture of ethylene glycol and a borate-containing composition which may be disodium octaborate tetrahydrate. In addition, the composition may be diluted with up to 50% by weight of water. However, the Bechgaard patent specifically teaches that such additions of diluent are disadvantageous because aqueous solutions of the active ingredient diffuse into the wood more slowly. Therefore, the amount of dilution should be minimized and, in fact, should not exceed 20% by weight. In fact, Bechgaard instructs that it is preferred that no water be present, to the extent possible. Bechgaard also suggest that it is known to impregnate wood with polyethylene glycol in order to make the wood more dimensionally stable (preventing shrinkage when the wood dries). See also Ember, *Preserving The Past*, C&E News 10, 12 (Nov. 14, 1988). It has also been suggested that minor amounts (i.e. about 2%) of fungicidal, insecticidal or fire retardant agents may be added thereto. These additives can include boron containing compounds. See Ember, *Preserving the Past* at Page 12. However, such uses involve polyalkylene glycols having a relatively high molecular weight, i.e., 1000 or higher.

Chapman et al. U.S. Pat. No. 3,305,298 relates to a protective treatment for wood. The treatment includes water, methanol, ethylene glycol, propylene glycol ethers, hologenated phenols, soluble borates, appears to be used as a buffering agent for the system. Chapman et al. requires the formation of a complex compound involving the organic mercury compounds, the borate ion and the hydroxylated compounds.

Ploquin U.S. Pat. No. 2,968,590 relates to a synergistic boric acid fungicidal composition which includes a boron containing composition, at least one organic compound having in its formula two identical or different radicals selected from OH, $NH_2$, NH and at least one organic or mineral base in an amount sufficient to make the pH of the product in the neighborhood of about pH 9. The organic compound may include "the glycols". All of the examples of Ploquin are limited to hexylene glycol or methylene glycol.

Stutz, U.S. published patent application B 848,336 relates to a wood preservative containing alkaline metal cyanides. More specifically, the alkaline metal cyanide is added to an alkaline borate buffered liquid fungicide concentrate of chlorophenates, and organic or inorganic salts of mercury, lead, titanium, copper and zinc. Furthermore, Stutz discloses the use of solvents which consist of alkanols having 1–4 carbon atoms which include a number of glycols identified at Column 2, lines 50–54.

Thornton et al., British Patent No. 937,766 relates to improvements in the treatment of wood and in the products obtained. The patent discloses a formulation which includes a boron containing active ingredient mixed with a small amount of a glycol containing from 2–8 carbon atoms, especially ethylene glycol. The amount of such ingredients should not exceed approximately 5%. Ethylene glycol, as used in the practice of the patent, is shown to be effective in concentrations of approximately 1%.

Short et al., U.S. Pat. No. 4,076,871 relates to a method of impregnating wood with boric acid or boric oxide by the use of boric acid esters of alcohols and thereafter hydrolyzing the esters. According to Short et al., it is well known that boric acid or boron oxide are effective as flame-proofing and fire-retardant agents for wood products.

See also, generally, Birkner et al., U.S. Pat. No. 3,099,598, Draganov, U.S. Pat. No. 3,378,381, Patel et al., U.S. Pat. No. 4,719,110, Goettsche et al., U.S. Pat. No. 4,761,179, Turner, U.S. Pat. No. 4,303,726, Boocock et al., U.S. Pat. No. 4,440,298 and Oberley, U.S. Pat. No. 4,373,010.

However; despite these and other wood preservative products and methods, nothing has been found to be completely satisfactory for a variety of reasons. For example, the composition of Champman et al. and Stutz include such compounds as alkaline metal cyanides and organic or inorganic salts of mercury. Such compounds are environmentally hazardous, many pose safety risks to persons and animals, and create difficult and expensive disposal problems.

The composition described in Bechgaard does not appear to suffer from these disadvantages. However, the viscous ethylene glycol solutions taught therein are not applicable to all situations and not suitable for a number of application techniques. See Johnson et al., A Test of "Boracol", A New Formulation Containing Borates, For the Diffusion Treatment of Lumber, project No. 02-17-43-396 dated May 1986, prepared for Forintek Canada Corp. at page 1. Furthermore, testing has established that the compositions of Bechgaard are not effective in either rapid or deep penetration. See Id. In fact, it has been found, completely contrary to the teachings of Bechgaard, that the presence of water in a borate delivery system is generally necessary for reasons other than a reduction of viscosity.

Finally, all of the treatments previously described are limited to timber, lumber and tree derived products. They are not applicable directly to living, growing trees to protect them from infestation.

OBJECTS AND SUMMARY OF THE INVENTION

It is therefore an object of the present invention to provide compositions useful for retarding and eradicating infestation in living trees and methods for applying such compounds to trees.

It is also an object of the present invention to provide for compositions which are useful for protecting cut timber, lumber, and other similar tree derived products from infestation, and which are useful in retarding or eradicating existing infestation. Methods of using such compositions are also an object of the present invention.

It is further an object of the present invention to provide solutions to the problems of wood infestation which are environmentally safe, economical and adapted for efficient application under a wide variety of circumstances. Without limitation, these include application to living trees, lumber and other tree derived products, existing structures and dwellings as well as within and around such structures and dwellings.

These and other objects will become readily apparent to those of ordinary skill in the appropriate art after a review of what follows.

In accordance with the objects just described, one aspect of the present invention is the provision of an environmentally safe composition for treating trees and tree derived products which includes at least one short chain polyalkylene glycol having an average molecular weight of between about 200 and 400, at least one short chain alkylene glycol, and a glycol soluble boron containing compound in an amount effective to retard or eradicate infestation.

In a particularly preferred embodiment in accordance with this aspect of the present invention, the aforementioned at least one short chain polyalkylene glycol is polyethylene glycol and is present in an amount of between about 4% and about 23% by weight; the aforementioned at least one short chain alkylene glycol is ethylene glycol and is present in amount of between about 27% and about 76% by weight and the aforementioned glycol soluble boron containing compound is disodium octaborate tetrahydrate and is present in an amount of between about 20% and about 50% by weight. In a more preferred embodiment in accordance with this aspect of the present invention, the polyethylene glycol has an average molecular weight of about 200 and is present in an amount of between about 8% and 15% by weight and more preferably between about 10% and 13% by weight. The ethylene glycol is present in an amount of between about 35% and about 62% and more preferably between about 45% and about 54% by weight. The disodium octaborate tetrahydrate is present in an amount of between about 30% and 50% by weight and more preferably between about 36% and about 45% by weight.

In a most preferred embodiment in accordance with this aspect of the present invention there is provided a composition including polyethylene glycol in an amount of about 11.9% by weight, ethylene glycol in an amount of about 47.5% by weight and disodium octaborate tetrahydrate in an amount of about 40.6% by weight.

Compositions according to this aspect of the present invention may also be expressed in terms of the ratio of boron to the mixed glycol carrier. Specifically, there may be provided an environmentally safe composition for treating trees and tree derived products which includes a mixed glycol having at least one short chain polyalkylene glycol with an average molecular weight of between about 200 and about 400, and at least one short chain alkylene glycol; and boron provided as a glycol soluble boron containing composition, in an amount effective to prevent or eradicate infestation.

The term "mixed glycol(s)" is intended to describe a mixture of at least one short chain polyalkylene glycol and at least one short chain alkylene glycol, preferably in a ratio of from about 1 part of said at least one polyalkylene glycol to about one part of said at least one alkylene glycol through about one part of said at least one polyalkylene glycol to about 20 parts of said at least one alkylene glycol.

By the term "boron provided as a glycol soluble boron containing composition", it shall be understood that elemental boron is not generally soluble, at room temperatures, in glycol or water based solvents. Therefore, the introduction of boron into these compositions requires the use of a complexed form thereof such as, for example, disodium octaborate tetrahydrate, borax, boric acid, the potassium, ammonium, and sodium salts of boric acid, and boric oxide. These glycol soluble boron containing compounds vary greatly in their boron content. However, to determine the proportions of ingredients useful in accordance with the present invention, one need merely calculate the amount of elemental boron to be delivered, regardless of the form the boron takes, and then select an appropriate amount of the desired boron containing composition to deliver that amount of boron. The ratio of mixed glycols can then be determined based on the amount of boron and type of boron containing species.

Furthermore, in accordance with one aspect of the present invention, the ratio of the boron provided as a glycol soluble boron containing composition to the mixed glycol carrier, ranges from about 1 part boron to about 5 parts mixed glycol to 1 part boron to about 20 parts mixed glycol. In a particularly preferred embodiment of the present invention, the ratio of boron, provided as a glycol soluble boron containing composition to the mixed glycols is about 1:6.6 to about 1:10.0 and in a most preferred embodiment the ratio is about 1:7.12 and the ratio of polyethylene glycol having an average molecular weight of about 200 to the ethylene glycols is about 1:4.

The compositions in accordance with this aspect of the present invention are viscous and generally too concentrated for economical application to timber. However, these formulations can be substantially diluted with a diluent, and preferably water, in order to form less viscous solutions having a wide range of applicability. Unlike compositions known in the art such as those described in Bechgaard, dilution can be accomplished without substantially sacrificing the speed and/or completion of penetration of the glycol soluble boron containing composition (active ingredient). In fact, it has been unexpectedly found that such dilutions are often essential in order to accomplish such penetration.

In addition to its ability to accommodate water, the compositions in accordance with this aspect of the present invention can be directly applied to live trees in order to provide in situ protection from insect infestation, fungal infestation and the like. It has been found that when the undiluted composition of this aspect of the present invention is administered directly to the interior of the tree, the active ingredient (boron containing compound) is dispersed through the tree. The tree is then protected from insect infestation, fungal infestation and the like. The tree so treated also has enhanced flame retardance. Furthermore, lumber manufactured from the tree so treated continues to exhibit resistance to infestation without additional treatment. In some cases, it may be advantageous to slightly dilute these formulations for direct application to living trees. In these cases, a dilution of about 1 part boron to about 4.3 parts water is preferred.

Other compositions useful in accordance with the present invention include glycerine and a boron containing active ingredient, with or without a short chain alkylene glycol such as ethylene glycol. These compositions are also useful for treating a live tree to prevent or eradicate infestation. This may be accomplished by the steps of: drilling a hole in the trunk of a tree to be treated; inserting into said hole adaptive means for accommodating the introduction of a solution; administering an environmental safe composition comprising boron provided as a glycerine soluble boron containing composition in an amount effective to prevent or eradicate infestation and glycerine in an amount effective to solubilize all of said boron.

Another method of treating a living tree to prevent or eradicate infestation in accordance with another aspect of the present invention includes the steps of: drilling a hole in the trunk of a tree to be treated; inserting into said hole adaptive means for accommodating the introduction of a solution; and administering an environmentally safe composition comprising boron provided as a glycerine and glycol soluble boron containing compound; provided in an amount effective to prevent or eradicate infestation and a mixture of glycerine and at least one short chain alyklyne glycol said mixture present in an amount effective to solubilize all of said boron.

In accordance with another embodiment of this aspect of the present invention there are provided compositions such as those just described which further include water. In one particular embodiment, the formulation in accordance with this aspect of the present invention includes at least one short chain polyalkylene glycol having an average molecular weight of between about 200 and 400, at least one short chain alkylene glycol, a glycol soluble boron containing compound in an amount effective to prevent or eradicate infestation, and water which is present in an amount up to about 10 times the volume of the combination of the other three ingredients; namely the at least one short chain polyalkylene glycol, the at least one short chain alkylene glycol and the glycol soluble boron containing compound.

In accordance with a more preferred embodiment of the present invention, the composition includes water in an amount of between about 0.5 and about 5 times the combined volume of the other three ingredients; namely the short chain polyalkylene glycol, short chain alkylene glycol, and the glycol soluble boron containing composition, and more preferably, between about 1 and about 4 times the combined volume of these three ingredients.

In a preferred embodiment in accordance with this aspect of the present invention, there is provided a composition including polyethylene glycol having an average molecular weight of about 200 which is present in an amount of between about 8% and 15% by weight, ethylene glycol which is present in an amount of between about 35% and about 62% by weight, disodium octaborate tetrahydrate which is present in an amount of between about 30% and 50% by weight, and water which is present in an amount up to about 10 times the volume of the combination of the other three ingredients.

In accordance with a more preferred aspect of the present invention, this composition contains water in an amount of between about 0.5 and about 5 times the volume of the other three ingredients; namely the polyethylene glycol, ethylene glycol and disodium octaborate tetrahydrate and more preferably, between about 1 and about 4 times the combined volume of these three ingredients.

In accordance with another more preferred embodiment of this aspect of the present invention there is provided a solution including polyethylene glycol in an amount of about 11.9% by weight, ethylene glycol in an amount of about 47.5% by weight, disodium octaborate tetrahydrate is present in an amount of 40.6% by weight and water which is present in an amount up to about 10 times the volume of the combination of the other three ingredients.

In accordance with a most preferred embodiment of this aspect of the present invention, there is provided a composition wherein polyethylene glycol is present in an amount of about 6.90%, ethylene glycol is present in an amount of about 27.54%, disodium octaborate tetrahydrate is present in an amount of 23.54% and water is present in an amount of about 42.01% by weight, based on the total weight of the composition.

When expressed in terms of parts of boron provided as a glycol soluble boron containing composition, the compositions in accordance with this aspect of the present invention may also include water. The amount of water included ranges from some amount greater than zero to an amount less than or equal to about 85.5 parts per part of boron provided as a glycol soluble boron containing compound. In a particularly preferred embodiment, the amount of water ranges from about 8.8 parts per part of boron provided as a glycol soluble boron containing compound to about 42.7 parts water per part of the aforementioned boron. In a more preferred embodiment the amount of water ranges from between about 8.8 and about 34.2 parts per part boron provided as in glycol soluble boron containing compound.

It has been unexpectedly found that the addition of water in a substantial amount to the compositions of the present invention including the glycol soluble boron containing compound, and a mixed glycol solution including at least one short chain polyalkylene glycol and at least one short chain alkylene glycol actually facilitates the deep, complete, and rapid penetration of the boron active ingredient into the treated wood (substrate). This is particularly unexpected in view of the teachings of, for example, Bechgaard which discloses a preferred composition of 40% active ingredient (disodium octaborate tetrahydrate) dissolved in 60% ethylene glycol. According to Bechgaard, the presence of water in combination with the aforementioned composition may be a necessary evil for reducing the viscosity of the resulting composition to allow it to be easily applied to tree derived products.

However, in the ideal situation according to the teachings of Bechgaard, no water is added. According to Bechgaard, as the amount of water increases above 20% by weight based on the weight of the carrier plus active ingredient (35 fl. oz. per gallon) there is a greater rate of precipitation of the active ingredient from solution and the impregnation rate and depth of penetration of the composition is compromised.

However, it has been found that the compositions taught by Bechgaard are, in general, no more efficacious than solutions of disodium octaborate tetrahydrate in water when applied to wood having a high water content, and only marginally superior when applied to wood having a low moisture content. See Johnson et al., Supra.

It has been unexpectedly found that water, when combined with a composition consisting of ethylene glycol and disodium octaborate tetrahydrate actually facilitates deep and rapid penetration of the boron containing active ingredient into the substrate. Dilutions of greater than about 50% by weight with water, unexpectedly, improves the delivery profile of the composition. Without wishing to be bound by any particular theory of operation, it is believed that the hygroscopic nature of ethylene glycol requires a significant amount of water and significant time period for efficacy. Therefore, and in accordance with one aspect of the present invention, there is provided a solution comprising ethylene glycol, disodium octaborate tetrahydrate, and greater than about 50% by weight of water.

Further, it has been advantageously found that the addition of a polyalkylene glycol to a formulation including a boron containing compound and an alkylene glycol allows for the incorporation of a substantial amount of water and that the resulting formulations excel in ways formerly unimaginable.

Not only do these compositions actually penetrate trees and tree derived substrate quickly and completely, but their stability is increased. For example, when the solutions including at least one short chain alkylene glycol, a glycol soluble boron containing compound, and at least one short chain polyalkylene glycol having an average molecular weight of between about 200 and about 400 are diluted 1:1 with water, greater stability is achieved. Further, it has been suprisingly and unexpectedly found that dilutions of 1:2 through about 1:5 with water, by volume, have greater stability than 1:1 dilutions by volume. Thus the addition of an increasing amount of water will actually add to the storage stability of the resulting mixture. Most importantly, however, and as previously described, by the use of the polyalkylene glycol and water containing solutions in accordance with the present invention a homogenous distribution of substantially all of the boron active ingredients applied to the tree derived product can be achieved. This penetration and distribution is achieved more rapidly than previously possible, particularly in lumber used in furniture, buildings, and the like, i.e. lumber having an approximate water content of between about 15% and 30%.

Without wishing to be bound by any particular theory, there are a number of reasons why solutions containing only ethylene glycol and a boron containing active ingredient, with or without a minor amount of diluent, may be ineffective. One such theory is that the higher concentrations of boron containing active ingredient found in the formulations in accordance with Bechgaard actually limit the potential rapid penetration thereof. Wood is known to have a generally low pH which hydrolyzes the borate containing ionic species into boric acid. Boric acid has a fairly low solubility, approximately 4% at STP. The result is that the boron containing active ingredient will precipitate out of the ethylene glycol carrier and form a crystalline barrier just under the surface of the wood. This crystalline barrier prevents additional borate containing solution from penetrating. Similar phenomenon have been reported by studies conducted at Oregon State University where it was determined that high concentrations of aqueous borate solutions result in a decrease penetration when compared to the penetration of lower concentration solutions. Thus, only in relatively high moisture content wood would the solutions of Bechgaard, with or without water dilution accomplish significant wood penetration.

Furthermore, when the compositions in accordance with Bechgaard are applied, evaporation of the volatile ethylene glycol and water begin immediately. This significantly limits the amount of carrier available for deep penetration and simultaneously shifts the equilibrium of the composition by increasing the relative concentration of boron containing compound. This may significantly increase the chance of boron precipitation within the wood. Finally, in low moisture content wood, the hygroscopic ethylene glycol has little moisture to use in drawing the active ingredient into the wood substrate. Therefore, while penetration may be greater than other known compositions in dry wood, it is still insufficient to provide deep penetration. This phenomena may be evidenced by the fact that the surface of wood to which the fourmulations of Bechgaard have been applied remain tacky to the touch for more than one week after application. However, if sufficient water is provided to conventional ethylene glycol/disodium octaborate tetrahydrate formulations, then, despite evaporation, sufficient moisture may be present to allow for deep penetration.

It has been unexpectedly and advantageously found that the addition of certain polyalkylene glycols and particularly polyethylene glycol having an average molecular weight of about 200, to the aforemention formulations facilitates the addition of significant amounts of water to the formulations. This has a number of advantageous consequences. Without wishing to be bound by any particular theory of operation, it is believed that the polyalkylene glycol stabilizes the active ingredient, even in the presence of a significant concentration of water. This helps prevent the precipitation of a crystalline boric acid and the formation of a penetration barrier. The presence of polyalkylene glycol also reduces the vapor pressure of the composition facilitating a decrease in the rate of evaporation of the water and ethylene glycol. More importantly, however, the polyalkylene glycol is believed to form a temporary moisture barrier which essentially prevent evaporation of the ethylene glycol and water thus preventing a shift in the solutions equilibrium. Furthermore, because these compositions in accordance with the present invention may include a significant amount of water, the compositions are particularly useful for application to dry wood. It is believed that sufficient water is provided to the dry substrate by the formulations of the present invention thus facilitating the deep penetration of the ethylene glycol and the boron containing composition carried thereby. The rapid penetration of the formulations of the present invention is evidenced by the fact that within about 1 hour following application to wood surfaces, the surface is not tacky.

The compositions in accordance with the present invention also provide the user with significant advantages. Consider, for example, the manufacturer of lumber who wishes to add a wood preservative to the material exiting his mill. Because the solutions in accordance with the present invention would be formulated with a relatively low viscosity, they may be applied as a spray, in an economically fine mist, or provided on a roller or brush which contact the wood as it moves along a conveyor. The presence of the polyalkylene glycol temporarily seals the formulations in accordance with the present invention within the wood allowing the penetration of the active ingredient to continue while the wood is in transit and, or, sitting in a lumber yard waiting for use. Because the presence of the temporary moisture barrier, the risk of the carrier solution drying up prior to deep penetration is reduced and therefore the need for re-application of preservatives is reduced. Finally, because the dilute solutions, in accordance with the present invention have a high degree of storage stability, the solutions can be pre-mixed and used at a considerably later date.

In accordance with another aspect of the present invention, there is provided a method for manufacturing an environmentally safe composition useful for preventing and eradicating infestation in a tree or tree derived product including the steps of charging at least one short chain polyalkylene glycol having an average molecular weight of between about 200 and about 400 and at least one short chain alkylene glycol to a sealable vessel; agitating the glycols preferably while raising their temperature; adding to the glycols an amount of at least one glycol soluble boron containing compound effective to prevent or eradicate infestation; agitating the glycols and the boron containing compound to produce a homogenous mixture; elevating the temperature of the mixture to between about 160° F. and 180° F.; and filtering the resulting mixture.

There is also provided a method of diluting the compositions made by the process just described by adding a measured amount of water to the filtered mixture resulting from the process described immediately above and mixing the diluted mixture to provide uniformity and eliminate cloudiness.

In accordance with another aspect of the present invention, there is provided a method of preventing or eradicating an infestation in a tree derived product including the steps of providing an environmentally safe composition which includes at least one short chain polyalkylene glycol having an average molecular weight of between about 200 and 400; at least one short chain alkylene glycol; and a glycol soluble boron containing compound in an amount effective to prevent or eradicate infestation; diluting the composition with water in amount of between about 0.50 and about 10.0 times the volume of the combination of the other three ingredients; mixing the resulting solution to provide uniformity and eliminate cloudiness; and applying the mixture to a surface of a tree or tree derived product.

In a preferred embodiment in accordance with the above described method, the short chain polyalkylene glycol is polyethylene glycol having an average molecular weight of about 200 and is present in an amount of between about 8% and 15% and more preferably 10% and 13% by weight based on the weight of the undiluted composition; that is based on the combined weight of the short chain polyalkylene glycol, short chain alkylene glycol and the glycol soluble boron containing composition. The short chain alkylene glycol is preferably ethylene glycol present in an amount of between about 35% and 62% and more preferably between about 45% and 54% by weight based on the weight of the undiluted composition. The glycol soluble boron containing composition is preferably disodium octaborate tetrahydrate present in an amount of between about 30% and 50% and more preferably in an amount of between about 36% and 45% by weight, based on the weight of the undiluted composition. Furthermore, in accordance with a preferred embodiment of this method, the amount of water provided ranges from between about 0.50 and 5 times the volume of the other three ingredients; namely, the polyethylene glycol, alkylene glycol and glycol soluble boron containing active ingredients and, more preferably between about 1 and 4 times the volume of the other three ingredients.

When placed in terms of parts boron there is provided a method of preventing or eradicating an infestation in a tree derived product comprising the steps of: providing an environmentally safe composition including a mixed glycol including at least one short chain polyalkylene glycol having an average molecular weight of between about 200 and about 400, and at least one short chain alkylene glycol; and boron provided as a glycol soluble boron containing composition in an amount effective to prevent or erradicate infestation; diluting said composition with water in an amount of between about 1 part boron to about 8.8 parts water to about 1 part boron to about 85.5 parts water; mixing the resulting solution to provide uniformity and eliminate cloudiness; and applying said mixture to a surface of a tree derived product.

In a preferred embodiment of this aspect of the present invention boron and the mixed glycols are present in an amount of between about 1 part boron to about 5 parts mixed glycol to about 1 part boron to about 20 parts mixed glycol and the mixed glycols include from about 1 part of the polyalkylene glycol to about 1 part of said alkalyne glycol to about 1 part of said polyalkylene glycol to about 20 parts of said alkylene glycol.

In a more preferred embodiment, the boron and mixed glycols are present in an amount of between about 1 part boron to about 6.5 parts mixed glycol to about 1 part boron to about 10 parts mixed glycol and the water is present in an amount of between about 8.8 parts per part boron to about 34.2 parts per part boron.

In a most preferred embodiment, the boron is present in an amount of about 1 part per 7.12 parts of the mixed glycol and the ratio of said polyalkylene glycol and the alkylene glycol is about 1:4 and the water is present in an amount of about 8.8 parts water to about 1 part boron. It is preferred that the polyalkylene glycol is polyethylene glycol having an average molecular weight of about 200 and the alkylene glycol is ethylene glycol.

The modes of application may include low pressure spraying, high pressure spraying, brushing, misting, immersion, injection, spreading, insertion, and pressure treatment.

In accordance with another aspect of the present invention, there is provided a method of treating a living tree to prevent or eradicate infestation comprising the steps of drilling a hole in the trunk of a tree to be treated; inserting into the hole adaptive means for accommodating the introduction of a solution; and administering an environmentally safe composition comprising at least one short chain polyalkylene glycol having an average molecular weight of between about 200 and about 400; at least one short chain alkylene glycol; and a glycol soluble boron containing compound in an amount effective to prevent or eradicate infestation to the tree through said adaptive means. The glycerine containing solutions in accordance with the present invention can also be used for direct application to trees.

The present invention also contemplates a tree so treated.

The present invention also includes, in accordance with another preferred embodiment, a composition of matter capable of providing protection against infestation and weathering including a hemogenous solution of at least one water emulsifiable polymer based weather sealant suitable for application to the surface of a tree derived product in an amount of about 80% to about 90% by weight; and an environmentally safe composition for treating tree derived products which include at least one short chain polyalkylene glycol having an average molecular weight of between about 200 and 400, at least one short chain alkylene glycol, and a glycol soluble boron containing compound present in an amount effective to prevent or eradicate infestation, wherein said environmentally safe composition is provided in an amount of between about 10% and 20% by weight.

DETAILED DESCRIPTION OF PREFERRED EMBODIMENTS

The compositions of the present invention include at least one short chain polyalkylene glycol having an average molecular weight of between 200 and 400. By short chain, it is understood that polyalkylene glycols having repeating units of between 2 and 4 carbon atoms in length are contemplated. In accordance with a preferred aspect of the present invention, polyethylene glycol is used, and in a more preferred embodiment in accordance with the present invention the polyethylene glycol has an average molecular weight of about 200.

Polyethylene glycols are readily available from a variety of commercial sources. One such source is Dow Chemical. For example, E200 is an ethylene glycol having an average molecular weight of about 200 and a chemical abstract registry number of 25322-68-3 which is available from Dow Chemical.

Polyethylene glycols and polyethylene glycols having an average molecular weight of about 200 are preferred over polypropylene glycols, polybutylene glycols and glycols having a higher molecular weight because of their generally lower relative viscosity and their general solubility in water. For example, E200 polyethylene glycol has an average viscosity of 187 centistokes at 32° F. and 40 centistokes at 77° F., whereas E300 polyethylene glycol has an average molecular weight of 300 and an average viscosity of 343 centistokes at 32° F. and 69 centistokes at 77° F. Furthermore, E200 is the most hygroscopic of the glycol series just described.

It is most preferred that polyethylene glycol having an average molecular weight of about 200 be used exclusively. However, the admixture of certain amounts of other average molecular weight polyethylene glycols and, indeed, other polyalkylene glycols is specifically contemplated. Such mixtures may be particularly useful when a particularly porous wood derived substrate is being treated.

The term "at least one short chain alkylene glycol" is intended to mean an alkylene glycol having a chain length of about 2 to about 4 carbon atoms. These would include, ethylene glycol, propylene glycol and butulene glycol. However, the most preferred compound for use in the present invention is ethylene glycol. Due to the relative volatility of ethylene glycol it may be useful, in accordance with the present invention, to use a mixture of ethylene glycol and one of the other short chain alkylene glycols disclosed herein.

The term infestation in accordance with the present invention is meant to include specifically infestation by insects and fungi. However, infestation may include stain molds such as *Ophiostoma Coerulem* or bacterial infestation as well. More specifically, the compositions in accordance with the present invention may be used to destroy and/or prevent the infestation of trees and tree derived products by Subterranean Termites: Reticulitermes, Heterotermes, Formosan Termites: Coptotermes, Dampwood Termites: Neotermes, Zootermopsis, Drywood Termites: Kalotermes, Incisitermes, Powder Post Beetles: Lyctidae, Bostrichidae, Anobiid Beetles: Anobiidae, Old House Borers Flat-headed Borers : Buprestadae, Ambrosia Beetles: Platypodidae, Scalytidae, Long-horned Beetles: Cerambycidae, Anobium; *Ambeodontius tristis*; Hylotrupes: *Lyctus brunneus; Anobium punctatum; Ambeodonius tristis; Hylotropes bajulus*, Carpenter Ants: Camponotus; White and Brown Wood Decay Fungi including: *Antrodia Sinuosa, Antrodia Xantha, Aspergillis Amstelodami, Aspergillus Niger, Aureobasidium Pullulans*, Basidomycete, *Bisporia Pusillas* 132, *Ceratocystis Pluriannulata, Ceratocystis Picea, Chaetomium Globosum Keinze, Coniophora Cerebella, Coniophora Olivacea, Coniophora Puteana, Fomes Lividus, Fomes Officinalis, Fomes Pini, Fomes Pinicola, Gloephyllum Abietinum, Gloephyllum Sepiarium, Gloephyllum Trabeum, Hericium Abietis, Heterobesidian Annosum, Lentinus Lepideus, Lenzites Trabea, Merulius Lacrymans, Ophiostoma Coeruleum, Paecilomyces Varioti*, Phialophora Sp., *Phialophora Fastigiata, Phialophora Haffmannii, Phialophora Heteromorpha, Phialophora Lignicola, Phialophora Lueto-Olivacea, Phoma Herbarum, Phoma Lanosa, Polyporus Abietinus, Polyporus Rugulosus, Polyporous Sulphureus, Polyporus Tomentosus, Polyporous Versicolor, Polystictus Versicolor, Poria Carbonica, Poria Incrassata, Poria Monticola* 698, *Poria Nigrescens* 4856, *Poria Placenta, Poria Subacida, Poria Vaillantii, Poria Vaporaria, Poria Xantha*, Rhinocladiella sp., *Sclerophoma Pityophila, Serpula Lacrymans, Sistotreme Brinkmenii, Stachbotrys Atra Corda, Stereum Abietirum*, Torulla Sp., *Trametes Lilacino-Gliva, Trametes Serialis, Trichocladium Asperum* and the like.

The term glycol soluble boron containing compound can be any boron containing compound, or elemental boron to the extent that such compounds are generally soluble in the glycol solutions in accordance with the present invention. "Generally soluble" is understood as including boron containing compositions capable of providing at least about 2% boron by weight to the undiluted mixed glycol solution.

In accordance with the present invention, the preferred glycol soluble boron containing compounds include disodium octaborate tetrahydrate, the potassium, ammonium, and sodium salts of boric acid, boric acid, "borax" and boric oxide and mixtures thereof. The term borax includes compounds having a general formula of $Na_2B_4O_7 \cdot xH_2O$ wherein "x" is a whole number from 0 to 10.

In accordance with one embodiment of the present invention, the amount of glycol soluble boron containing compound mixed with the at least one short chain polyalkylene glycol and the at least one short chain alkylene glycol is an amount sufficient to effectively prevent or eradicate infestation. According to Dr. Susan Jones of the U.S. Department of Agriculture, as little as 100 parts per million of boron is efficacious against, for example, dry wood termites. (Report of Dr. Susan Jones of U.S.D.A., Forest Products Research Laboratories, Gulfport, Mississippi, presented at the Conference on Urban Entomology, College Park, Md., February 1990). Other species of insects and fungi may require a greater concentration of boron for complete efficacy. See also: "Feeding and Survival of Subterranean Termites on Souther Pine Pressure-Treated with TIM-BOR, First Progress Report", J. Mauldin & R. Beal, USDA Forest Service, Southern Forest Experiment Station, 4510, FS-50-4502-7.230, January 1987; "Termite Resistance of Treated Wood in an Above Ground Field Test, Part II", A. Preston, et al., The International Research Group on Wood Preservation, Document No. IRG/WP/1300, May 25, 1986; "Integrated Protection Against Lyctid Beetle Infestations IV. Resistance of Boron-Treated Wood to Insect and Fungal Attack", L. Williams & T. Amburgy, Forest Products Journal, 37, No. 2, 10 (1987); "Laboratory Studies of Termite Resistance III", F. Gay, et al., Commonwealth Sci. Ind. Res. Org. (Australia), Div. Entomology, Tech. Paper No. 4, (1958); "The Threshold Level of Boron Preservatives Against Attack by the Dry-Wood Termite *Cryptotermes Domesticus-Kalotermitedea*", A. Tisseverasinghe & M. Jayatilleke, Sri Lanka Forester, 12, No. 2, 89 (1975); "Efficacy of Boron Salts Against Attack by Subterranean Termites", M. Ortiz, Inf. Tec. Inst. For., Santiago No. 21, 130 (1965).

It has been found, however, that a concentration of 500 parts per million (ppm) boron (2400 ppm DOT active) is generally effective for preventing or eradicating a broad spectrum of infestation. This is approximately the amount of boron provided by a solution comprising polyethylene glycol in an amount of about 11.9% by weight ethylene glycol in an amount of about 47.5% by weight and disodium octaborate tetrahydrate present in an amount of 40.6% by weight when diluted 1:1 by volume with water when applied to a 6"×12" board, having a density of about 30 lbs/cu.ft. and a moisture content of about 15%. (Application is to each side of the board, including the ends, until the point of run-off.)

For certain species of insect such as Formosan termites and certain types of fungi, for example *Aspergillus amstelodami* more concentrated boron may be required. As such, it may be necessary to apply two coats of the boron containing compounds of the present invention to achieve optimum efficacy. Generally speaking, however, the amount of glycol soluble boron containing compound should range from about 20% to about 50% by weight of the undiluted formulation and more preferably between about 30% and about 50% by weight thereof.

In another more preferred embodiment in accordance with the present invention, the amount of the glycol boron containing compound should range from about 36% and about 45% and is, most preferably, about 40.6% by weight.

The amount of at least one short chain polyalkylene glycol having an average molecular weight of between about 200 and about 400 useful in the practice of the present invention may range from between about 4% and about 23% by weight of the undiluted composition. In a more preferred embodiment in accordance with the present invention, the amount of the polyalkylene glycol may range between about 8% and 15% by weight of the undiluted composition and even more preferably between about 10% and 13% thereof. In a most preferred embodiment in accordance with the present invention, the at least one short chain polyalkylene glycol having an average molecular weight of between about 200 and about 400 is present in an amount of 11.9% by weight of the undiluted formulation.

The amount of polyalkylene glycol added depends upon a number of factors including, for example, the method by which the formulation is to be applied. A far more viscous solution may be accommodated by the use of a brush or other applicator when compared to a spray or fine misting type of applicator. Therefore, the amount of polyalkylene glycol may be greater when applied by a brush. The amount of polyalkylene glycol may also be determined, to a certain extent, by the types of polyalkylene glycols used. If the polyalkylene glycol is a mixture of, for example, polyethylene glycol having an average molecular weight of about 200 and polypropylene glycol, then less may be required or accommodated because of the generally higher viscosity of the resulting mixed polyol. The porosity of the substrate to which the formulation is applied may also play a role in determining the amount of polyalkylene glycol used in the formulation.

In accordance with the present invention, the at least one short chain alkylene glycol may be provided in an amount of between about 27% and about 76% by weight of the undiluted formulation, and more preferably between about 35% and about 62% by weight thereof. In a more preferred embodiment in accordance with the present invention, the alkylene glycol is present in an amount of about 45% to about 54% by weight of the undiluted formulation and most preferably, the amount of alkylene glycol useful in accordance with the present invention is about 47.5% by weight of the undiluted formulation.

The compositions according to the present invention may also be expressed in terms of the ratio of boron to the mixed glycol carrier. As previously discussed, elemental boron is generally insoluble in glycols and therefore is provided as a glycol soluble boron containing composition. By knowing the amount of boron intended for delivery, one can select an amount of boron based upon the glycol soluble boron containing composition to be used and adjust the amount of that composition based, in part, upon its individual boron content. By determining the amount of boron to be provided, the amount of mixed glycols necessary to act as carrier can be determined and their ratio selected.

Therefore, in accordance with one aspect of the present invention, it is preferred that the ratio of boron provided as a glycol soluble boron continuing compound to the mixed glycol solution containing at least one short chain polyalkylene glycol having an average molecular weight of between about 200 and about 400 and at least one short chain alkylene glycol be between about 1 part boron to about 5 parts mixed glycol to about 1 part boron to about 20 parts mixed glycol. The mixed glycol should include from about 1 part of polyalkylene glycol to about 1 part of the alkylene glycol to about 1 part of the polyalkylene glycol to about 20 parts of the alkylene glycol.

More preferably, the mixed glycols are present in an amount of between about 6.5 and 10 parts per part boron provided as a glycol soluble boron containing composition. In a particularly preferred embodiment in accordance with this aspect of the present invention, the polyalkylene glycol is a polyethylene glycol having an average molecular weight of about 200, the alkylene glycol is ethylene glycol and the amount of boron contained in the composition is about 1 part per 7.12 parts of the mixed glycols and the ratio of the polyethylene glycol to the ethylene glycol is about 1:4. In a preferred embodiment in accordance with the present invention the undiluted composition should include between about 4.0 and 10.5% boron and in a most preferred embodiment, the composition should include about 8.32% boron by weight.

In general, the undiluted formulations of the present invention can be made by both batch and continuous processes. One method of manufacturing the compositions in accordance with the present invention includes the steps of providing an amount of at least one short chain polyalkylene glycol and at least one short chain alkylene glycol and charging these glycols to a sealable vessel; agitating the mixed glycols and, preferably, raising the temperature thereof. The glycol soluble boron containing compound is then added to the vessel under sufficient agitation to break up all lumps such that a homogeneous mixture is formed. The temperature of the mixture is then raised to between approximately 160° and 180° F. with agitation. Finally, the solution is removed from the vessel and filtered.

Another advantageous method of producing the undiluted formulations in accordance with the present invention includes simultaneously metering the correct proportions of the short chain polyalkylene glycol, short chain alkylene glycol and glycol soluble boron containing compound into a mixing vessel, whereby the materials are mixed at a constant rate in order to form a homogeneous solution.

Means are provided for drawing off a predetermined amount of the homogeneous mixture from the mixing vessel at a fixed rate. The mixture is then fed into a series of static mixers/heat exchangers, each of which is independently temperature controlled, and the material is eventually heated to a temperature of between about 160° F. and 180°F. by the end of the process line. The solution is then filtered and packaged.

In accordance with another aspect of the present invention, the aforementioned formulations may be diluted with a diluent, preferably water. There are a number of factors which play a role in determining the amount of dilution useful for a given application. For example, and as previously discussed, target infestation toxicity may play a large role. The more boron required for efficacy, the less the dilution and/or the greater number of applications. Furthermore, the density of the substrate may have some effect on the penetrability of the active ingredient. Generally, the more dense the substrate the more dilute the solution should be.

Other factors include the size and ratio of surface area to total volume of the tree or tree derived products to be treated. Generally, the higher the surface area to volume ratio, the greater the allowable dilution. For example, lumber having a cross section of 6"×12" can be effectively treated by the solutions of the present invention when diluted 1:1 with water. For lumber having a cross section less than 6"×12", more dilute solutions may be useful and more cost effective while delivering a sufficient amount of boron.

The moisture content of the wood being treated also has a role in determining dilution. obviously the higher moisture content of the substrate to be treated, the less dilution that is required. Other factors include whether the lumber is so-called dimensional lumber or is a composite such as plywood and whether or not the wood is used in furniture. Water is known to raise the grain of the wood and thus less dilute solutions may be useful for application to furniture.

The application method will also play a role in determining the solution's appropriate dilution. If a paste is desirable, the dilution should be minimized. Another factor which may be considered is whether or not the compositions in accordance with the present invention are going to be used with a top coat or sealant. In this eventuality it is preferred that the solution be more dilute. Another factor to be considered is the speed of penetration required. For example, the formulation of the present invention, when diluted 1:4 with water and applied to dimensional lumber having a 6"×12" cross section and an approximate density of 30 lbs./cu.ft. will provide about 500 ppm of boron throughout the tree derived substrate. This concentration may not be sufficient for completely eradicating an infestation of certain insects and/or fungii. However, the rate of penetration of this formulation is significantly greater than even a 1:1 dilution of the same formulation. This rapid initial treatment, or "knock down", may be quite useful under certain conditions.

Dilution can, under certain circumstances, be as much as 100 times the weight of the undiluted composition. However, for most purposes, the compositions in accordance with the present invention can be diluted by the addition of up to about 10 times the volume thereof.

In a highly preferred embodiment in accordance with the present invention, the undiluted formulation is diluted in a 1:1 volume ratio with water, providing a solution that is about 6.90% polyalkylene glycol, 27.54% alkylene glycol, about 23.54% glycol-soluble, boron-containing compound, and 42.01% water by weight, based upon the total weight of the composition. It has also been found that dilution factors, by volume, ranging from between about 1:0.5 (formulation/water) and 1:5 (formulation/water) are desirable and dilution factors of between about 1:1 (formulation/water) and 1:4 (formulation/water) are most preferred. In fact, it has been found that when the compositions of the present invention are diluted with between about 2 and about 4 times their volume of water, the storage stability and the rate of penetration actually increase. This is true even when comparison is made to formulations diluted 1:1 with water.

Therefore, a preferred composition in accordance with the present invention includes between about 6.90% and about 3.05% polyethylene glycol, between about 27.54% and about 12.19% ethylene glycol, between about 23.54% and about 10.40% disodium octaborate tetrahydrate, and between about 42.01% and about 74.35% water by weight based upon the total weight of the composition.

When such diluted solutions are described in terms of the parts of boron present as a glycol-soluble boron-containing composition, the aforementioned composition includes about one part boron per 7.12 parts mixed glycols, and the ratio of the polyethylene glycol to the ethylene glycol is about 1:4. The amount of water is between about 8.8 and about 34.2 parts per part boron. Dilutions of about 1:1 equate to about 8.8 parts water per part boron, dilutions of 1:2 equate to about 17.1 parts water per part boron, dilutions of about 1:3 equate to about 25.6 parts water per part boron, and a dilution of 1:4, by volume, equates to about 34.2 parts water per part boron. A dilution of about 1:5 by volume equates to about 42.7 parts water per part boron and a dilution of about 1:10 by volume equates to about 85.5 parts water per part boron.

TABLE I

| Dilution | % DOT | % EBC | Boron:Water (parts) |
| --- | --- | --- | --- |
| 1.1 | 23.5 | 4.8 | 1:8.8 |
| 1:2 | 16.6 | 3.47 | 1:17.1 |
| 1:3 | 12.8 | 2.68 | 1:25.6 |
| 1:4 | 10.4 | 2.17 | 1:34.2 |
| 1:5 | 8.77 | 1.83 | 1:42.7 |
| 1:10 | 4.92 | 1.03 | 1:85.5 |

The formulation diluted in accordance with Table I included about 11.9% by weight polyethylene glycol having an average molecular weight of about 200 (PEG 200), ethylene glycol in an amount of about 47.5% by weight (EG), and disodium octaborate tetrahydrate in an amount of about 40.6% by weight (DOT). All weights reflect the undiluted formulation. % EBC is the % of equivalent boron content by weight.

In general, dilution may be accomplished by measuring a known volume of the undiluted compositions of the present invention and placing same into a clean container. A measured amount of diluent, preferably water, is then added to the container. The use of warm water can assist in the mixing process. The mixture is then stirred or agitated until the solution is uniform and all cloudiness disappears.

In accordance with one aspect of the present invention there is provided a solution comprising at least one short chain alkylene glycol, prefeeably ethylene glycol, a glycol soluble boron containing composition and water present in an amount of at least 50% by weight based on the weight of the other two compositions. The ratio of the alkylene glycol to the boron containing composition should be from about 10:1 to about 1.5:1. However, in a preferred embodiment in accordance with this aspect of the present invention, there is produced a solution comprising approximately 40% by weight of disodium octaborate tetrahydrate and 60% by weight of ethylene glycol, diluted with greater than about 50% by weight of water, based on the combined weight of the ethylene glycol and the disodium octaborate tetrahydrate. The amount of water diluent can range from about 50% by weight to about 1000% (10:1 ratio). Formulations in accordance with this aspect of the present invention may lack the stability of the polyethylene glycol and water containing formulations previously described, and, due to evaporation, will not continue to penetrate a wood substrate for as long a period of time. However, these formulations may be suitable for certain applications.

In accordance with another aspect of the present invention there is provided a solution which includes, at very least, a boron containing active ingredient such as those previously described and glycerine. Specifically, there is provided an environmentally safe composition for treating trees and tree derived products comprising boron provided as a glycerine soluble boron containing composition in an amount effective to prevent or eradicate infestation and glycerine in an amount effective to solubilize all of said boron. Generally speaking, the glycerine is present in an amount of from about 5 to about 20 parts per part boron and, in a preferred embodiment, the boron provided as a glycerine soluble boron containing composition is disodium octaborate tetrahydrate. In a more preferred embodiment, the formulation in accordance with this aspect of the present invention is a composition having 40.6% by weight of disodium octaborate tetrahydrate with the balance being glycerine. This composition may also be diluted with up to 10 times the volume of water or approximately up to 85.5 parts water per part boron in the diluted formulation. Preferably, however, the formulation as diluted with from 1 to about 4 times its volume with water or is diluted with between 8.8 and 34.2 parts water per part boron.

In another aspect of the present invention there is provided a forumulation similar to that just described except that a portion of the glycerine is replaced by at least one short chain of alkylene glycol such as, for example, ethylene glycol. Specifically, the present invention provides an environmentally safe composition for treating trees and tree derived products which includes boron provided as a glycol and glycerine soluble boron containing compound or composition in an amount effective to prevent or eradicate infestation and; a mixture of glycerine and at least one short chain alkylene glycol. The mixture of the glycol and glycerine should be present in an amount effective to solubilize all of the boron. Preferably, the mixture of glycerine and glycol is present in an amount of from about 5 to about 20 parts per part boron and the ratio of glycol to glycerine ranges from about 4:1 to about 1:4. In a preferred aspect of the present invention, the boron provided as a glycerine and glycol soluble boron containing compound or composition is disodium octaborate tetrahydrate and is present in an amount of about 40.6% by weight, the short chain alkyene glycol is ethylene glycol which is present in an amount of 47.5% by weight and the glycerine is present in an amount of about 11.9% by weight.

These formulations may similarly be diluted by up to about 10 times their volume with water.

The glycerine and glycerine/glycol solutions of the present invention have pronounced disadvantages with regard to their application as compared to the polyalkylene glycol and water based formulations previously described. Generally speaking, they are more viscose, tacky, and somewhat more difficult to work with. However, they may be manufactured and used in the same way as the alkylene glycol/boron containing compound and polyalkylene glycol/ alkylene glycol/boron containing compounds of the present invention. Furthermore, because glycerine is less expensive than certain glycols and poses absolutely no threat to the environment, it may be applicable in areas of particular environmental sensitivity or where cost is critical. Furthermore, due to its tackiness, it is preferable to use the glycerine based formulations of the present invention through an injection application method such as injecting these formulations into wood pre-treated with a weather sealant, and the like, as well as live trees.

A number of ingredients or additives may be added to any of the formulations of the present invention without departing from this invention and without materially altering the characteristics of the formulations. These ingredients include: surfactants such as TRITON X-100 manufactured by Rohm & Haas, present in amount of from about 0.01% to about 1% or AMP-95, manufactured by Angus Chemicals present in the amount of about 0.001% to about 0.4%; colorants including pigments such as AQUASPERSE manufactured by Nuodex, Inc. present in the amount of about 0.25% and 5.0% or dyes such as Pylam dyes, produced by Pylam Prod Co., Inc. present in the amount of from about 0.1% to about 2%; Mildicides such as BUSAN M-11 present in the amount of from about 1% to 10%, BL-1067 present in the amount from about 0.5% to about 5% BUSAN 1009, present in an amount from about .5% through about 5% and BUSAN 30WB, present in an amount from about .5% to about 5% (all manufactured by Buckman Labs.); Spreader/ stickers such as TRITON B-1956 manufactured by Rohm & Haas present in the amount from about 0.01% to about 1%; thickening agents such as polyvinyl alcohol manufactured by Air Products present in the amount of from about 0.001% through 1% by weight and TEXIPOL 13-510, manufactured by Scott Bader, present in the amount of from about 2.5% to about 5%; film forming agents such as AIRFLEX 500, manufactured by Air Products, and present in an amount of between about 5% and about 50%; UNOCAL 1018 manufactured by UNOCAL present in an amount of about 5% to about 50%; water repellents such as 85 ADDITIVE manufactured by Dow Corning, present in an amount of about 1% to 10% and stablizers such as sodium sulphite available through Fisher Scientific in an amount of about 1% through 5%.

Various formulations in accordance with the present invention may be used for a wide variety of purposes. These include use as an insecticide applied to the bark or under the bark of living trees, to the siding or exposed or unexposed wood members of dwellings or structures, decks, furniture, etc. It may also be added to eradicate or to prevent infestation by fungi, as previously described. The formulations in accordance with the present invention may be applied to wood being used for construction prior to its sale and/or prior to its leaving the milling or other manufacturing facility.

It should be remembered when reviewing the following that it should be possible to accomplish total penetration and distribution of boron in an amount of about 500 ppm by the application, to dimensional lumber having a cross section of 6"×12" of one application of the preferred formulations prepared in accordance with this invention, when diluted 1:1 with water to each side of the lumber, including the ends, to the point of run off. However, it is often impossible to gain access to each side of lumber when it is part of an existing structure. In that case, it may be necessary to repeatedly coat a lesser number of sides to obtain the full distribution of the active material. Or, if the wood has a higher surface area and/or cross section, the application to only a limited number of sides may be adequate.

In other cases, access may be limited to a small area resulting from a hole drilled through, for example, a wall in a house. In that eventuality, it may be appropriate to inject the formulation of the present invention, directly into the wood. In such cases, 1 gallon of 1:1 diluted injected solution should provide 500 ppm's of boron when applied to about 400 board feet of wood. (One board ft. equals 1"×12"×12" wood or 144 in.$^3$)

More specifically, the uses of the compositions in accordance with the present invention include the remedial treatment of tree derived products for the control of subterranean, formosan, drywood and dampwood termites, carpenter ants, old house borers, anobiid and other wood boring beetles and wood decay fungi. This may be accomplished by the application of a diluted solution of the composition of the present invention to the point of runoff to infested areas and to those areas susceptible to infestation to include all exposed wood. Two coats of diluted solutions are applied in accordance with the present invention when heavily infested areas are being treated, waiting at least 20 minutes between applications. When practical, diluted solutions can be injected into beetle holes, termite and carpenter ant galleries, and decay pockets, and the like.

Infested wood flooring can be treated by spray or brush application. It will generally be necessary in such cases to remove any existing finish by sanding or the like prior to application. Diluted solutions are applied in accordance with the present invention at a rate of approximately 1 gallon per 500 square feet of floor surface, thus providing boron in an amount sufficient to control or prevent infestation. At least 72 hours are permitted to then elapse after treatment and before applying a new floor finish coating. If at that part the surface remains tacky or a residue is evident, the treated surface can be wiped with a damp cloth and allowed to dry prior to applying the finish coat.

For treating wall studs and wood members which are not accessible by conventional application methods, the solution can be sprayed into voids and channels in damaged wood and through small holes drilled into walls and baseboard areas. A sufficient amount of coarse spray should be used in order to cover the area to the point of runoff.

While it is possible that older wood boring beetle larvae already present in the wood at the time of treatment may burrow deep into the wood ahead of the diffusing borate and emerge sometime after treatment, this will generally not occur frequently enough to cause structural damage to the wood.

Another use for the formulations of the present invention is in the pretreatment of tree derived products and/or structures for prevention of subterranean and formosan termites in crawl spaces, basements and slabs. This treatment can also serve as a primary treatment for the control of subterranean termites.

For buildings with crawl spaces and basements, diluted solutions in accordance with the present invention can be applied to the point of runoff to all wood surfaces in crawl spaces and basements, including sills, plates, all floor joists, piers, girders, and subfloors, as well as wood which is exposed to vertical access from the soil. In this case, base plates and all interior and exterior studs shall be so treated.

For buildings on slabs, diluted solutions in accordance with the present invention can be applied to the point of runoff to all wood which is in contact with the slab, including all base plates, as well as studs in both the interior and exterior walls. In that case, it shall be insured that all sill plates and wood contacting garages and porches be treated. In cases where access is limited to one or two sides of a wood member, two coats of diluted solutions can be applied to the exposed surfaces in accordance with the present invention. At least 20 minutes should be allowed to elapse between such applications.

Still another use of the formulations of the present invention is as a pretreatment to provide total protection from subterranean, formosan, drywood and dampwood termites, carpenter ants, old house borers, anobiid and other wood boring beetles and wood decay fungi. This may be accomplished by applying diluted solutions in accordance with the present invention to all wood surfaces, ends and cracks at junctures to the point of runoff. Such applications in areas that are particularly susceptible to attack should be treated most carefully. These include sills, plates, floor joists, piers, girders, subfloors and any wood that is exposed to vertical access to the floor. All base plates and studs on exterior walls should be so treated, as used as studs surrounding any high moisture areas such as bathrooms, kitchens, and laundry rooms. For buildings built on slabs, all wood in contact with the slab, including all interior studs, should be treated.

In attics, all exposed wood should be treated, including ceiling joists, trusses, top plates, soffits, rafters, and roof decking. It should also be insured that all sill plates and wood contacting garages and porches are treated. In areas where access is limited to one or two sides of a wood member, two coats of diluted solutions should be applied to the exposed surfaces in accordance with the present invention. Again, at least 20 minutes should be permitted to elapse between applications.

The compositions in accordance with the present invention may also be used for the post-construction treatment of basements and crawl spaces by applying diluted solutions in accordance with the present invention to the point of runoff to all wood surfaces including sill plates, piers, girders, subfloors, floor joists and any wood exposed to vertical access from the soil. Two coats of diluted solutions in accordance with the present invention should be applied to wood where access is limited to one or two sides of wood members, such as sills and plates on exterior walls. At least 20 minutes should again be permitted to elapse between applications.

The compositions in accordance with the present invention are also useful for the treatment of exterior wood surfaces such as decks, sheds, and siding. The foregoing may be accomplished by applying the diluted solutions in accordance with the present invention only to bare wood or to wood surfaces where an intact water repellent is not present. If necessary, paint or finish can be removed prior to application. Diluted solutions in accordance with the present invention should be applied to the point of runoff to all wood surfaces. Two coats of diluted solutions in accordance with the present invention should be applied to infested areas, and to those surfaces where access is limited to one or two sides of wood members (siding, flooring, etc.). The formulations should not be applied in rain or snow. Thus, exterior wood surfaces should not be exposed to rain or snow for at least 48 hours after treatment. If inclement weather is expected, exterior treated surfaces should be protected with a plastic tarp.

Exterior wood surfaces which have been treated with solutions in accordance with the present invention may require a topcoating with a water resistant finish such as paint or exterior stain. It is important to allow treated wood to completely dry (at least 48 hours) before applying any protective topcoat.

Furthermore, the compositions of the present invention may also be used in the treatment of log structures by applying diluted solutions in accordance with the present invention only to bare wood or to wood surfaces where an intact water repellent is not present. Diluted solutions in accordance with the present invention should thus be applied to the point of runoff to all interior and exterior wood surfaces. On round logs 10" or greater in diameter and rectangular logs larger than 6"×12", two coats of solution should generally applied. At least one hour should elapse between such applications. Two coats of solutions in accordance with the present invention should also be applied to log ends, notches, corners and sill logs, and once again it should not be applied during rain or snow. Exterior wood surfaces should not be exposed to rain or snow for at least 48 hours after treatment, and if inclement weather is expected, the exterior treated surface should be protected with a plastic tarp. Firewood may also be treated with the formulations in accordance with the present invention to prevent and or eradicate infestation. This may be accomplished by spraying the diluted formulations of the present invention directly onto a wood pile making sure to cover or coat all exposed wood surfaces. It is preferred that the wood so treated be allowed to dry prior to burning. More efficient treatment may be accomplished by the removal of existing bark prior to application of the aforementioned formulations.

In another advantageous application, the formulations of the present invention may be used to treat decrative bark mulch to protect it from infestation.

In all of the foregoing, it is particularly advantageous to use a formulation comprising polyalkylene glycol having an average molecular weight of about 200 present in an amount of about 6.90%, ethylene glycol present in an amount of about 27.54%, disodium octaborate tetrahydrate present in an amount of 23.54%, and water present in an amount of about 42.01% by weight, based on the total weight of the composition diluted 1:1 with water. Formulations diluted with 2–4 volumes of water may also be particularly useful.

Additionally, compositions in accordance with the present invention may be directly applied to the interior of trees and subsequently dispersed throughout the tree to provide the tree with in situ protection from infestation and for the eradication of already existing infestation. These compositions include the polyalkylene glycol/alkylene glycol/water/active formulations in accordance with the present invention as well as the formulations which include glycerine. Advantageously, a tree so treated which is then cut down at a later time will generally not require additional treatments with the compositions of the present formulation. Furthermore, the formulations of the present invention may be added to wood to impart a measure of flame retardancy thereto. Thus, it should be understood that while this description is primarily directed to compositions and methods of using these compositions to prevent and/or eradicate infestation, they may also be used to impart flame-retardancy.

The compositions of the present invention may be applied in a wide variety of ways. A number of these methods will now be discussed in more detail.

Firstly, these compositions can be applied as a spray solution, via either low or high pressure (airless) sprayers.

When using low pressure portable sprayers, the diluted solutions in accordance with the present invention are poured into the tank of a low pressure, garden type sprayer (such as the SP1 Knap Sack Sprayer available from Pagliai-Powell Imports, Inc. 12016 Wilshire Blvd., Los Angeles, Calif., and all wood surfaces, including the ends, can then be sprayed. The solution is then applied until it begins to run off (the point of run off). If two or more coats of solutions in accordance with the present invention are desired, at least 20 minutes should elapse between applications. Exterior treated surfaces should be protected from rain for at least 48 hours.

When using high pressure or high volume sprayers, an amount of clean water should be added to the holding or mixing tank as is necessary to attain the desired final solutions in accordance with the present invention. Recirculation of the water is initiated, and the solutions in accordance with the present invention are then slowly added thereto. When the solution is uniform, spraying may begin. All wood surfaces, including the ends, should be sprayed. The solution is applied until it begins to run off. If two or more coats of solutions in accordance with the present invention are desired, at least 20 minutes should again elapse between applications. Exterior treated surfaces should be protected from rain for at least 48 hours.

An amount of clean water should be added to the holding or mixing tank as is necessary to attain the desired final solutions in accordance with the present invention. Recirculation of the water should be initiated, and the solutions in accordance with the present invention can then be slowly added. When the solution is uniform, spraying may begin. Wood members should be passed through the spray system, making sure that all surfaces are coated with the solutions in accordance with the present invention. Excess solution may be removed by high pressure air, vacuum or by allowing members to drip. Recovered solution may be reused.

The compositions of this invention may also be applied by means of a brush-on solution. In doing so, the hands should be protected with solvent resistant gloves. Diluted solutions in accordance with the present invention are then brushed onto all surfaces of the wood to be treated, including the ends. The solution is applied until it begins to run off, and it is again not applied in the rain or snow.

Yet another application method includes the application of a fine mist onto wood surfaces or other material using a "fogging" device. In this case, diluted solutions in accordance with the present invention are placed into a fogging device such as FOGMASTER Model 6208 or FOGMASTER Model 7401 manufactured by Fogmaster Corp., Deerfield Beach, Fla. The fogging device is placed into a confined area, where spraying may well be inconvenient or impractical. When turned on, the fogging device will thus emit a fine mist of diluted solutions in accordance with the present invention, which will adhere to all surfaces present in the confined area.

Another method of application includes immersing material into a vat or tank of the solutions in accordance with the present invention. The wood is dipped into the diluted solutions in accordance with the present invention for at least about two minutes. Bundled wood members should be stickered in order to allow the solution to cover all wood surfaces in the bundle. One dip application should be sufficient for all wood members up to and including 12 inches in diameter. Wood should be removed from the dip tank and held above the tank for at least two minutes in order to allow the excess solution to drip back into the tank. The treated wood can be protected by storing under a roof or by covering with a tarp for a period of at least about 48 hours.

Yet another method involves injecting the solution into a wood member or live tree. In this case, a solution in accordance with the present invention is injected into the tree by drilling a hole into the base (within 3 feet of the ground or at a convenient point in the tree derived product) of the tree which is infested or subject to future infestations or decay. These holes can be made using a drill equipped with a bit which is ¼ to 1 ½ inches in diameter. The solution in accordance with the present invention is then inserted into the drilled cavity by means of a tube connected to a reservoir containing the solution. The reservoir can be an inverted plastic container, which is attached to the tree (i.e. strapped thereto) above the drilled hole, or suspended above the drill hole in tree derived products. The tube can then be inserted into the tree through a hole adaptive means for accommodating the introduction of a solution which may be a tapered stopper and the like which is cut to match the diameter of the drilled hole.

It will be beneficial to insert removable stoppers in order to reuse the assembly and to avoid contamination when the tree is harvested.

Another method of application involves spreading a paste or suspension onto the surface of a wood member, live tree or material to be treated. In this case, the solution in accordance with the present invention can be formed into a paste by mixing a thickening agent with the concentrated solution in accordance with the present invention. The paste is applied to the wood surface by spreading with a brush, roller, or trowel. On live trees, it may be beneficial to remove sections of the bark prior to application.

Application can also take place by using traditional pressure treatment methods. Current pressure treatment technology is used for imparting protection to wood via copper, chrome, and arsenic salts which mandates the application of these chemicals in a water based solution. The only available borate chemicals other than solutions in accordance with the present invention registered for use as wood preservatives are dry powders, which must be dissolved prior to use. The use of dry powders within the pressure treatment industry is not looked upon with favor since existing equipment is designed to handle only aqueous solutions or suspensions. Dilute versions of solutions in accordance with the present invention can thus be used as a direct replacement for existing treatment compositions.

The procedures for pressure treating wood are largely standarized and may be used with little or no modification. One such standard useful in accordance with the present invention is AWPA Standard C1-88 which is within the jurisdiction of American Wood-Preservers' Association Subcommittee T-1 and which is hereby incorporated by reference.

The compositions of the present invention may also be used in conjunction with stains, paints, primers and other weather sealants to provide long lasting protection from infestation and the elements. This is particularly useful when the tree derived products (wood, cellulose, etc.) to be treated is regularly exposed to the elements. Such products are often incorporated in building exteriors, decks, outdoor furniture, docks, boats, and other exposed structural supports.

One method of using the compositions of the present invention with weather sealants is to first coat the wood to be treated with the composition of the present invention. Then, after about 48 hours, the surface to which the compositions of the present invention were applied can be coated a second time with a conventional weather sealant, paint, primer, stain, or the like. This method is particularly useful in conjunction with sealant compositions which are incompatible with the compositions of the present invention.

However, where weather sealant compositions are compatible with the compositions of the present invention, it is possible, and advantageous, to admix or otherwise provide a consolidated solution which can be applied in one coat. One particular group of resinous based compounds which are compatible with the formulations of the present invention include the acrylics, styrene-acrylics, vinyl acrylics, vinyl acrylic/ethylene or other emulsion polymer systems. Stains, paints, or weather sealants of this type can have added thereto an undiluted solution in accordance with the present invention in an amount ranging from about 10 to about 20% by weight of the finished formula. It is preferred that the pH of the resulting product be between about 4.5 and about 9.5. Furthermore, it is important that surfactants, dispersants, pigments, and other additives contained within the sealant be tested for individual compatibility with compositions of the present invention. In this context, it is important that the amount of water in the system (including the water in the wood) be considered. An unduly high water concentration may affect the stability of the compositions of the present invention. It is also important that the coating be tailored such that the weather sealant does not dry too quickly. The compositions of the present invention requires about 20–30 minutes to begin the process of impregnating the substrate. However, should the weather resistant coating begin to dry or cure prior to that time, the active ingredient of the present invention may be entrapped and encapsulated therein.

In a more preferred embodiment, the combined weather selant composition includes an emulsion polymer system based sealant in combination with the basic undiluted formulations of the present invention. This includes a formulation including a homogenous solution of at least one water emulsifiable polymer based weather selant suitable for application to the surface of a tree derived product, in an amount of about 80% to about 90% by weight, and an environmentally safe composition for treating tree derived products which include at least one short chain polyalkylene glycol having an average molecular weight of between about 200 and 400, at least one short chain alkylene glycol, and a glycol soluble boron containing compound present in an amount effective to prevent or eradicate infestation, wherein said environmentally safe composite is provided in an amount of between about 10% and 20% by weight. More preferably, the at least one short chain polyalkylene glycol is polyethylene glycol and even more preferably polyethylene glycol having an average molecular weight of about 200. The amount of polyalkylene glycol should range from about 4% to about 23% and preferably between about 8% and about 15% and more preferably between about 10% and about 13% by weight of the basic undiluted formulation, i.e. without including the weight of the weather sealant.

The short chain alkylene glycol is preferably ethylene glycol which is present in an amount of between about 27% and about 76% by weight and preferably between about 35% and 62% by weight, and more preferably between about 45% and 54% by weight of the basic undiluted formulation.

The glycol soluble boron containing composition is preferably disodium octaborate tetrahydrate which is present in an amount of between about 20% and 50% by weight, and preferably between 30% and about 50% by weight and more preferably between about 36% and 45% by weight of the basic undiluted formulation.

Most preferably, the environmentally safe composition to be combined with the emulsion based polymeric weather sealant should include about 11.9% PEG 200, 47.5% EG and 40.6% DOT by weight.

As previously described, another method of applying the formulations of the present invention is particularly well suited for wood which has already been weather treated. In such cases, the injection of solutions of the present invention may avoid the need to strip off existing weather protection.

Of course, it may be possible to deliver a sufficient amount of the formulations of the present invention to a piece of wood by injection in only one spot, it is preferred that a plurality of injections be used equally spaced throughout the treated wood, based on the dimensions of wood, target infestation, dilution factor, wood porosity and desnity, ease of access and the like.

The foregoing will be better understood with reference to the following examples. These examples are for purposes of illustration. They are not to be considered limiting as to the scope and nature of the present invention:

EXAMPLE I

Batch Process
Batch #1014 MFG. 11-16-89

| Ingredients | Mfg. By | Lot # |
|---|---|---|
| 1) Ethylene Glycol Cas #107-21-1 | Unocal | 03161390 |
| 2) PEG E-200 Cas #025322-68-3 | Dow | 0104900 H |
| 3) TIMBOR Disodium Octaborate Tetrahydrate | U.S. Borax | 9-J110-28 |

| Formula: | Pounds | Gallons | Wt. % | Raw Material |
|---|---|---|---|---|
| | 772.00 | 83.01 | 47.50 | Ethylene Glycol |
| | 194.00 | 20.70 | 11.90 | PEG E-200 |
| | 660.00 | 37.07 | 40.60 | TIMBOR |
| Totals | 1626.00 | 140.73 | 100.00 | |

All ingredients weighted on WEIGHT TRONIX 5000# cap. Scale Model #DS-05 (±. 1% accuracy)

Batch made in 150 gal. cap. Brighton Mixer with variable speed air motor/twin paddle-type agitators on single shaft. (304 stainless steel) Closed Lid-top entering agitator. Steel skirt to contain heat. Vented. Ser. No. 211.

Nalco propane heater 250,000 btu/hr. Model #2 E427.
1. Mixer was placed (empty) on scale and weight tared off.
2. Ethylene glycol (772 lbs.) added from 2 55 gal. drums. Weight tared.
3. Peg E-200—(194 lbs.) was added—removed mixer from scale.
4. Mixer started to blend glycol components (200 rpm approx.).
5. propane heater placed under mixer and ignited-(1/4 output) approx 75,000 BTU's/hour.
6. After heating glycol mixture to 112° F. heat removed.
7. 14–50 lbs. bags TIMBOR\ on pellet placed on scale and weight recorded (750.4 lbs.).
8. Added 12 (50 lbs.) bags TIMBOR\ (approx. 25 min e.t.)(approx. 600 lbs. TIMBOR\).
9. Empty bags (12) and pallet with 2 full bags returned to scale-weight recorded is 155.6 lbs.
10. Calculated remaining TIMBOR\ to add—750.4—155.6= 594.8 added 660–594.8=65.2 lbs TIMBOR\—weighed and added to batch.
11. Returned heater—full output 250,000 Btu/hr. heated for 43 min. to 184° F. Removed heat—continued agitation for approx. 10. min to even out possible hot-spots in mix. Product allowed to cool to 120° F. for pkg. (about 12 hrs.).
12. Product was then pumped into HDPE 5 gal. containers with Wilden model M-8 diaphragm pump and Rosedale Model 8 filter housing with 150 micron nylon mesh filter.

Batch number was assigned as 1014. Composite sample analyzed by Micro-Macro International, Inc., Athens, GA to contain 8.76% boron or 41.9% equivalent disodium octaborate tetrahydrate.

EXAMPLE II

Preserving Stain—Clear

In a Brighton mixer were combined 27.11 wt. % of UNOCAL 1018 (Styrene-acrylate) (polymer emulsion) and 21.92 wt. % of deionized water (diluent). These were then mixed for three minutes. Then a UV package (17.0% TINUVIN 1130 U.V. light inhibitor, 34.14% TINUVIN 292 U.V. light inhibitor, 48.78% TEXANOL solvent) in an amount of about 1% by weight of the formulation was added along with 1.7% by weight of glycol ether EB (cosolvent) and were mixed for about 10 min. Thereafter, the following were added under continuous agitation.

0.036 wt. % Colloids 681° F. (defoamer)
0.50 wt. % Daxad 30 (pigment dispersement)
0.001 wt. % Triton X-405 (surfactant)
32.30 wt. % D.I. Water (diluent)
2.72 wt. % Ethylene Glycol (retards film formation)
0.01 wt. % Kathon Lx 1.5% (in-can preservative)
3.70 wt. % AQUABEAD 418E (water repellant usage)
9.00 wt. % Undiulted formulation of the present invention comprising insecticide coating Machine colorant as needed not to exceed 5% by weight;
Mix until homogeneous 10–15 min.

An important restriction of coating formulation is the viscosity and drying time of the system. The component will preferentially penetrate the substrate compared to the balance of the liquid components, but drying time of the coating must allow time for this to occur; typically at least 30 min. to one hour.

EXAMPLE III

The formulations of the present invention have been found to be particularly useful for the treatment of low and moderate moisture content wood. Wood found in the home and typically constructed structures usually has a moisture content of between about 15% and about 30%. In wood with such a moisture content, the formulations of the present invention have a much higher rate of penetration than conventional formulation such as those disclosed in Bechgaard. As noted previously, within 24 hours of the application of the formulations of the present invention to general structural lumber, and usually within about 1 hour after application, the wood so treated is dry to the touch. Wood treated with the solutions according to Bechgaard remain tacky to the touch for in excess of one week. The penetration rate is also evident from the following example which uses wood having a moisture content even lower than commonly encountered:

1. Three formulations in accordance withe present invention were prepared from an initial composition including:
PEG 200—11.9% by weight undiluted, EG-47.5% by weight undiluted, disodium octaborate tetrahydrate—40.6% by weight undiluted. This formulation was then diluted as follows:
(a) 1:1 (50 ml formulation/50 ml H$_2$O) approx. 4.8% B content by weight or 1 part B per 8.8 parts water;
(b) 1:2 (33 ml formulation/66 ml H$_2$O) approx. 3.5% B content or about 1 part B per 17.1 parts water; and
(c) 1:3 (25 ml formulation/75 ml H$_2$O) approx. 2.7%B conent or about 1 part B per 25.6 parts H$_2$O.

(d) 100 ml of BORACOL—40% weight disodium octaborate tetrahydrate and 60% ethylene glycol, undiluted (approx. 8.36% B content by weight) was prepared for comparison.

2. Each solution was placed in a separate Petri dish.

3. 10 inch lengths of white pine 1½"x¾" stock (moisture content of 11%, ½ inch into the wood using a Delmhorst Moisture Meter, Model, RC-2) were sectioned into two equal lengths of 5 inches each.

4. Each five inch length was labeled, then placed, fresh cut end down, in the Petri dishes. Five samples were placed into each solution.

5. Wood samples were left in the solutions for 24 hours.

6. At the end of 24 hours the wood samples were removed from the solutions and air dried for 8 days.

7. Approximately ¼" was then removed from the face of each wood sample with an electric planer.

8. Each sample was then sprayed with a curcumin indicator which can detect boron at levels equal to or greater than 0.2% boric acid equivalent. (Edlund, M.L. 1982, Utilization of curcumin for detection of presence of boron in wood. Inter. J. of Wood Preserv. 2(3):133.)

9. Three representative wood samples subjected to each solution were selected and photographs showing the penetration of the boron constituent of each product were taken.

The length of boron penetration of each wood sample was measured and recorded. The average length of penetration for each set of samples was then calculated.

| Solution | Average Length of Boron Penetration |
| --- | --- |
| (d) | 0.28 inches |
| (a) | 0.40 inches |
| (b) | 0.65 inches |
| (c) | 0.75 inches |

EXAMPLE IV

Penetration Test of Pine Log

An eight inch diameter, three foot long, white pine log was determined to have a moisture content of approximately 28%. The basic formulation in accordance with the present invention represented by (a) in EXAMPLE III was applied by brush to the circumference of the log. No. solution was applied to the ends.

Two days later another coat was applied by brush. Again, nothing was applied to the ends.

After four weeks a cross section sample was taken from the middle of the log about 1½ feet from the end. The cross section sample was air dried for 10 days, then sprayed with curcumin indicator in order to determine borate penetration across the grain.

The borate was found to be uniformly distributed across the entire cross section sample. There did not appear to be any zone of high borate concentration vs low concentration. It was clear that the borate consitituent of the formulation in accordance with the present invention had penetrated, across the grain, to the very center of the log.

EXAMPLE VI

1. ¾ inch plywood panels containing 7% moisture content were treated on one side with a solution containing PEG 200—11.9% by weight, EG-47.5% by weight and DOT—40.6% by weight diluted 1:1 with an equal volume of water at application rates of 400 square feet per gallon (board feet) (1 coat), 200 square feet per gallon (2 coats) and 133 square feet per gallon (3 coats).

2. Two weeks after application cross section samples were analyzed.

| Treatment | % B* | % BAE* | Calculated as Boric Acid Equivalent |
| --- | --- | --- | --- |
| 1 coat @ 400 sq. ft./gal. | 0.048 | 0.27 | |
| 2 coats @ 400 sq. ft./gal. | 0.086 | 0.49 | |
| 3 coats @ 400 sq. ft./gal. | 0.13 | 0.74 | |

*by weight -- wood density approx. 30 lbs./cu. ft.

EXAMPLES VII–IX

The following formulations were prepared in accordance with the general procedure of EXAMPLE I except as otherwise noted.

Batches 1012–1014

660 lbs. of TIMBOR\ brand disodium octaborate tetrahydrate available from U.S. Borax (lot 9-J11D-18) (98% DOT/2% inert)

194 lbs. of PEG 200 (Mfg. by Dow)

772 lbs. of EG (Mfg. by Dow)

The mixture was heated for 2 hours until it reached 180° F.

Boron Analyses (% Boron by Weight)

Batch 1012—8.2

Batch 1013—8.6

Batch 1014—8.8

EXAMPLES X–XII

The following formulations were prepared in accordance with the general procedure of EXAMPLE I, except as otherwise noted.

Batches 1015–1017

660 lbs. of TIMBOR\ (Lot 9-J11D-28)

194 lbs. of PEG 200 (Mfg. by Dow)

772 lbs. of EG (Mfg. by Dow) (weights rounded up)

The mixture was heated for 4 hours at about 180° F.

Boron Analysis (% Boron by Weight)

Batch 1015—9.59

Batch 1016—9.80

Batch 1017—7.63

EXAMPLE XIII

The following formulation was prepared in accordance with the general procedure of EXAMPLE I except as otherwise indicated.

Batch 1018

663 lbs. of TIMBOR\ (Lot No.9-J11D-28)

194 lbs. of PEG 200 (Mfg. by Dow, Lot No. 01049004H)

772 lbs. of EG (Mfg. by Dow, Lot No. C5079,OMP)

The mixture was heated for 4 hours at about 180° F.

Boron Analyses (% Boron by Weight)

Batch 1018—8.87

EXAMPLE XIV

The following formulation was prepared in accordance with the general procedure of EXAMPLE I, except as otherwise indicated.

Batch 1019
  860 lbs. of TIMBOR\ (47.09% by weight (Lot No. 9-J11D-28)
  194 lbs. of PEG 200 (10.62%) (Mfg. by Dow, Lot No. 0104900H)
  772 lbs. of EG (Mfg. by Dow, Lot No. 050790MP)
  The formulation was liquid at STP.
Boron Analysis (% Boron by Weight)
  Batch 1019—10.12 (Theoretical 9.64)

EXAMPLE XV

The following formulation was prepared in accordance with the general procedure of EXAMPLE I, except as otherwise indicated.
Batch 1021
  770 lbs. of TIMBOR\ (44.35% by weight) (Lot No. 9-E31E-16)
  194 lbs. of PEG 200 (Mfg. by Dow, Lot No. 0104900H)
  772 lbs. of EG (Mfg. by Dow)
  A new agitator was used and set at the middle of the shaft. The glycols were heated to 112° F. prior to adding the TIMBOR\.
Boron Analysis (% Boron by Weight)
  Batch 1021—8.33% (Theoretical 9.08% B)

EXAMPLE XVI

The following formulation was prepared in accordance with the general procedure of EXAMPLE I, except as otherwise indicated.
Batch 1022
  700 lbs. of TIMBOR\ (42.94% by weight)(Lot No. 9-E31E-16)
  160 lbs. of PEG 200 (9.81%) (Mfg. by Dow, Lot No. 0104900H)
  770 lbs. of EG (47.24% (Mfg. by Dow, Lot No. 0316032790)
  The glycol was warmed to 110° F. prior to the addition of the TIMBOR\ and then heated until 180° F.
Boron Analyses (% Boron by Weight)
  Batch 1022—8.32 (Theoretical 8.795)
  Because these examples were run on an open system, it is believed the about 0.5% of the boron or about 8 lbs./batch is lost through volitilization. To compensate, as in Batch 1022, additional initial TIMBOR\ may be added.

EXAMPLE XVII

Dilution stability test (at 68° F. and 50% rel. humidity) 6 fl. oz. of various formulations were placed in open polystyrene containers (8 oz.) with wooden tongue depressers submerged in the formulation to provide a nucleous for crystal formation.

| | Dilution Ratio (H₂O) | | | | | | | |
|---|---|---|---|---|---|---|---|---|
| | 1:1* | 2:1* | 3:1* | 4:1* | 5:1* | 1:0.2** | 1:1** | A |
| B | | | | | | | | |
| Day 1 H | N | N | N | N | N | S | N | N |
| Day 2 | S | N | N | N | N | S | S | N |
| Day 3 H | M | N | N | N | N | M | S | N |
| Day 4 H | H | N | N | N | N | H | M | N |
| Day 5 H | V | S | N | N | N | H | H | N |
| Day 6 | V | M | N | N | N | | | |
| Day 7 | V | H | N | N | N | | | |
| Day 8 | V | H | N | N | N | | | |
| Day 9 | V | H | N | N | N | | | |
| After 10 days | V | V | N | N | N | | | |

*Solution used includes 11.9% PEG 200, 47.5% EG, and 40.6% DOT.
**Solution used was BORACOL[ ](40% DOT, 60% EG)
A - Solution of 10% DOT in water
B - Solution of 20% DOT in water
N = No Sedimentation    H = Heavy Sedimentation
S = Slight Sedimentation    V = Very Heavy Sedimentation
M = Moderate Sedimentation

EXAMPLE XVIII 40.6% TIMBOR\ by weight (Lot No. 9-J-11D-28)
47.5% Ethylene Glycol (Mfg. by Dow, Lot No. 0361390)
11.9% Glycerine U.S.P. Grade 99% Mfg. by Dow, Lot No. TB850919-4)

The formulation was prepared on a lab-type hot plate with a magnetic stirrer SYBRON/THERMOLYNE (Model No. BP-13115) in a 500 ml beaker. The ingredients were heated under agitation to 180° F. with a petri dish cover over the beaker and using a teflon coated stir-bar. (1.5")

EXAMPLE XIX

The following formulation was prepared in accordance with the general procedure of EXAMPLE XVIII except as otherwise noted.
  49.6% TIMBOR\ by weight (Lot No. 9-J11D-28)
  59.4% glycerine U.S.P. Grade 99% Mfg. by Dow (Lot No. TB880919-4)

EXAMPLE XX

The following formulation was prepared in accordance with the general procedure of EXAMPLE XVIII except as otherwise noted.
  40.6% TIMBOR\ by weight (Lot No. 9-J11D-28)
  11.9% PEG 300 (Mfg. by Dow Lot No. TB880723)
  47.5% EG (Mfg. by Dow)

EXAMPLE XX1

A mixture of 40.6% by weight of TIMBOR\ and 59.4% by weight of glycerine (99%) U.S.P. grade from Dow was prepared by charging both ingredients to a vessel and heating with constant agitation on a laboratory hot plate/stirrer 280° F. After the mixture reached 180° the mixture was allowed to cool.

A pine block 3½"×10"×1½" had four holes ⅛" in diameter and ¾" deep drilled into it at 1" intervals. The aforementioned mixture was injected into the holes (undiluted) with a syringe and allowed to diffuse at ambient conditions for four weeks. The block was then sawed in half lengthwise through all four holes and sprayed with a calorimetric indicator. Boron penetration of greater than .2% BAE was indicated by a red color. Penetration of this concentration averaged approximately ¾" in distance from the injection sites.

The principles, preferred embodiments and modes of operation of the present invention have been described in the foregoing specification. The invention which is intended to be protected herein, however, is not to be construed as limited to the particular embodiments disclosed, since these are to be regarded as illustrative rather than restrictive. Variations and changes may be made by others without departing from the spirit and scope of the invention.

What is claimed is:

1. A composition for treating tree derived products which results from heating a mixture comprising:
    at least one short chain polyalkylene glycol having an average molecular weight of between about 200 and about 400;
    at least one short chain alkylene glycol; and
    a glycol soluble boron containing compound in an amount effective to prevent or eradicate infestation and wherein said at least one short chain polyalkylene glycol is polyethylene glycol; and said at least one short chain alkylene glycol is propylene glycol and said glycol soluble boron containing compound is selected from the group consisting of borax, boric acid, potassium, ammonium and sodium salts of boric acid, boric oxide and disodium octaborate tetrahydrate which is present in an amount of between about 20% and about 50% by weight.

2. The composition of claim 1 wherein said polyethylene glycol is present in an amount of between about 4% and about 23% by weight and said propylene glycol is present in an amount of about 27% and about 36% by weight.

3. The composition of claim 2 wherein said polyethylene glycol is present in an amount of between about 10% and about 13% by weight, said propylene glycol is present in an amount of between about 45% and about 54% by weight and said disodium octaborate is present in an amount of between about 35% and about 45% by weight.

4. The composition of claim 3 wherein said polyethylene glycol is present in an amount of about 11.9% by weight, said propylene glycol is present in an amount of about 47.5% by weight and said disodium octaborate tetrahydrate is present in an amount of about 40.6% by weight.

5. The composition of claim 1 further comprising water.

6. The composition of claim 5 wherein said water is present in an amount of up to about 10 times the volume of the combination of said at least one polyethylene glycol, said propylene glycol and said glycol soluble boron containing compound.

7. The composition of claim 6 wherein said water is present in an amount of between about 0.5 and about 5 times the volume of said polyethylene glycol, propylene glycol and glycol soluble boron containing compound.

8. The composition of claim 2, further comprising water.

9. The composition of claim 3, further comprising water.

10. The composition of claim 4, further comprising water.

11. A composition for treating tree derived products which results from heating a mixture comprising:
    a mixed glycol including polyethylene glycol having an average molecular weight of between about 200 and about 400 and propylene glycol; and
    boron provided as a glycol soluble boron containing compound in an amount effective to prevent or eradicate infestation.

12. The composition of claim 11 wherein said mixed glycol includes from about 1 part of said polyethylene glycol to about 1 part of said propylene glycol to about 1 part of said polyethylene glycol to about 20 parts of said propylene glycol.

13. The composition of claim 12 wherein said boron provided as a glycol soluble boron containing compound is selected from the group consisting of disodium octaborate tetrahydrate, borax, boric acid, potassium, ammonium, and sodium salts of boric acid, and boric oxide.

14. The composition of claim 13 wherein said boron and said mixed glycols are present in an amount of between about 1 part boron to about 6.5 parts mixed glycol to about 1 part boron to about 10 parts mixed glycol.

15. The composition of claim 14 wherein the amount of said boron is about 1 part per 7.12 parts of said mixed glycol and the ratio of said polyethylene glycol and said propylene glycol is about 1:4.

16. The composition of claim 14 wherein said glycol soluble boron containing compound is disodium octaborate tetrahydrate.

17. The composition of claim 11 further comprising water.

18. The composition of claim 17 wherein said water is provided in an amount of up to 85.5 parts per part of boron.

19. The composition of claim 13 further comprising water in an amount of up to about 85.5 parts per part of boron.

20. The composition of claim 16 further comprising water in an amount of between about 8.8 parts per part boron to about 85.5 parts per part boron.

21. The composition of claim 20 wherein said water is present in an amount of between about 8.8 parts per part boron to about 34.2 parts per part boron.

22. A composition for treating tree derived products resulting from a mixture comprising:
    polyethylene glycol having an average molecular weight between about 200 and about 400; propylene glycol; and a glycol soluble boron containing compound in an amount effective to prevent or eradicate infestation and wherein said glycol soluble boron containing compound is selected from the group consisting of borax, boric acid, potassium, ammonium and sodium salt of boric acid, boric oxide and disodium octaborate tetrahydrate and is present in the amount of between about 20% and about 50% by weight, and wherein said composition is capable of dilution with water in the amount between about 0.5 and about five times the combined volume of said polyethylene glycol, propylene glycol and said soluble boron containing compound.

23. A composition for treating tree derived products comprising:
    a mixed glycol including polyethylene glycol having an average molecular weight of between about 200 and about 400 and propylene glycol; and
    boron provided as a glycol soluble boron containing compound in an amount effective to prevent or eradicate infestation.

24. The composition of claim 23 wherein said mixed glycol includes from about 1 part of said polyethylene glycol to about 1 part of said propylene glycol to about 1 part of said polyethylene glycol to about 20 parts of propylene glycol.

25. The composition of claim 23 wherein said glycol soluble boron containing compound is selected from the group consisting of disodium octaborate tetrahydrate, borax, boric acid, potassium, ammonium, and sodium salts of boric acid and boric oxide.

26. The composition of claim 23 further comprising water.

27. The composition of claim 24 wherein said boron and said mixed glycols are present in an amount of between about 1 part boron to about 5 parts mixed glycol to about 1 part boron to about 20 parts mixed glycol.

28. The composition of claim 22 further comprising water in an amount of between greater than 0.5 and about 5 times volume of said polyethylene glycol, propylene glycol and glycol soluble boron containing compound.

29. The composition of claim 5 wherein said water is included in said composition after said polyethylene glycol, propylene glycol, and glycol soluble boron containing compound have been combined.

30. The composition of claim 17 wherein said water is included in said composition after said polyethylene glycol, propylene glycol, and glycol soluble boron containing compound have been combined.

31. The composition of claim 26 wherein said water is included in said composition after said polyethylene glycol, propylene glycol, and glycol soluble boron containing compound have been combined.

32. A composition for treating tree derived products comprising:
a mixed glycol including polyethylene glycol having an average molecular weight of between about 200 and about 400 and propylene glycol;
boron provided as a glycol soluble boron containing compound in an amount effective to prevent or eradicate infestation; and
water.

33. The composition of claim 32 wherein said water is present in an amount of between about 0.5 and about 10 times the combined volume of said polyethylene glycol, propylene glycol, and glycol soluble boron containing compound.

34. A composition for treating tree derived products which results from agitating a mixture comprising:
at least one short chain polyalkylene glycol having an average molecular weight of between about 200 and about 400;
at least one short chain alkylene glycol; and
a glycol soluble boron containing compound in an amount effective to prevent or eradicate infestation, wherein said at least one short chain polyalkylene glycol is polyethylene glycol; and said at least one short chain alkylene glycol is propylene glycol, and said glycol soluble boron containing compound is selected from the group consisting of borax, boric acid, potassium, ammonium and sodium salts of boric acid, boric oxide and disodium octaborate tetrahydrate which is present in an amount of between about 20% and about 50% by weight.

35. The composition of claim 34 further comprising water present in an amount of between about 0.5 and about 10 times the combined volume of said polyethylene glycol, propylene glycol, and glycol soluble boron containing compound.

36. The composition of claim 35 wherein said water is included in said composition after said polyethylene glycol, propylene glycol, and glycol soluble boron containing compound have been combined.

37. A composition for treating tree derived products which results from agitating a mixture comprising:
a mixed glycol including polyethylene glycol having an average molecular weight of between about 200 and about 400 and propylene glycol; and
boron provided as a glycol soluble boron containing compound in an amount effective to prevent or eradicate infestation.

38. The composition of claim 37 further comprising water present in an amount of between about 0.5 and about 10 times the combined volume of said polyethylene glycol, propylene glycol, and glycol soluble boron containing compound.

39. The composition of claim 38 wherein said water is included in said composition after said polyethylene glycol, propylene glycol, and glycol soluble boron containing compound have been combined.

* * * * *